United States Patent
Moyo et al.

(12)

(10) Patent No.: US 9,913,901 B2
(45) Date of Patent: Mar. 13, 2018

(54) COMBINATION THERAPY FOR TREATING HER2-POSITIVE CANCERS

(71) Applicant: Merrimack Pharmaceuticals, Inc., Cambridge, MA (US)

(72) Inventors: Victor Moyo, Ringoes, NJ (US); Bart S. Hendriks, Belmont, MA (US); Thomas Wickham, Groton, MA (US); Elena Geretti, Cambridge, MA (US); Joseph G. Reynolds, North Andover, MA (US); Christopher W. Espelin, Belmont, MA (US)

(73) Assignee: Merrimack Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/650,250

(22) PCT Filed: Dec. 3, 2013

(86) PCT No.: PCT/US2013/072941
§ 371 (c)(1),
(2) Date: Jun. 5, 2015

(87) PCT Pub. No.: WO2014/089127
PCT Pub. Date: Jun. 12, 2014

(65) Prior Publication Data
US 2016/0250328 A1    Sep. 1, 2016

Related U.S. Application Data

(60) Provisional application No. 61/810,254, filed on Apr. 9, 2013, provisional application No. 61/732,736, filed on Dec. 3, 2012.

(51) Int. Cl.
| | |
|---|---|
| *A61K 39/395* | (2006.01) |
| *A61K 9/127* | (2006.01) |
| *A61K 31/704* | (2006.01) |
| *A61K 47/10* | (2017.01) |
| *A61K 47/24* | (2006.01) |
| *C07K 16/32* | (2006.01) |
| *A61J 1/16* | (2006.01) |
| *A61K 9/00* | (2006.01) |
| *C07K 16/28* | (2006.01) |
| *C07K 16/40* | (2006.01) |
| *A61K 47/68* | (2017.01) |
| *A61K 47/69* | (2017.01) |
| *A61K 39/00* | (2006.01) |

(52) U.S. Cl.
CPC .......... *A61K 39/39558* (2013.01); *A61J 1/16* (2013.01); *A61K 9/0019* (2013.01); *A61K 9/127* (2013.01); *A61K 9/1271* (2013.01); *A61K 31/704* (2013.01); *A61K 47/6871* (2017.08); *A61K 47/6913* (2017.08); *C07K 16/2863* (2013.01); *C07K 16/32* (2013.01); *C07K 16/40* (2013.01); *A61K 2039/507* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,593,622 A | 1/1997 | Goto | |
| 5,676,971 A | 10/1997 | Goto | |
| 5,846,458 A | 12/1998 | Goto | |
| 6,210,707 B1 | 4/2001 | Papahadjopoulos et al. | |
| 6,214,388 B1 | 4/2001 | Benz et al. | |
| 7,022,336 B2 | 4/2006 | Papahadjopoulos et al. | |
| 7,135,177 B2 | 11/2006 | Benz et al. | |
| 7,244,826 B1 | 7/2007 | Marks et al. | |
| 7,449,184 B2 | 11/2008 | Allison et al. | |
| 7,507,407 B2 | 3/2009 | Benz et al. | |
| 7,846,440 B2 | 12/2010 | Schoeberl et al. | |
| 7,871,620 B2 | 1/2011 | Benz et al. | |
| 7,892,554 B2 | 2/2011 | Kensington et al. | |
| 2005/0084524 A1 | 4/2005 | Martin et al. | |
| 2005/0276822 A1 | 12/2005 | Wiseman et al. | |
| 2006/0258656 A1 | 11/2006 | Matteucci et al. | |
| 2006/0269542 A1 | 11/2006 | Hjortsvang et al. | |
| 2007/0082856 A1 | 4/2007 | Gianni et al. | |
| 2008/0108135 A1 | 5/2008 | Marks et al. | |

(Continued)

FOREIGN PATENT DOCUMENTS

| | | |
|---|---|---|
| WO | 1997038731 A1 | 10/1997 |
| WO | 2006116107 A2 | 11/2006 |

(Continued)

OTHER PUBLICATIONS

Violette, P.D., et al., J Am. Board Fam. Med., 25: 111-119, 2012.*
Kinsinger, L.S., et al, Ann Intern. Med. 137: 59-67, 2002.*
Gong, S.J., et al., Cancer Letters, 214: 215-224, 2005.*
Meza-Junco, J., et al., Expert Opinion on Biological Therapy, 9(12): 1543-1551, 2009.*
Neve, Richard M., et al. "Biological Effects of Anti-ErbB2 Single Chain Antibodies Selected for Internalizing Function", Biochemical and Biophysical Research Communications, 280 (2001), pp. 274-279.

(Continued)

*Primary Examiner* — Misook Yu
*Assistant Examiner* — Anne L Holleran
(74) *Attorney, Agent, or Firm* — Honigman Miller Schwartz and Cohn LLP; Fernando Alberdi; Cynthia M. Bott

(57) ABSTRACT

Methods for treating cancer patients with HER2-positive tumors are disclosed. The methods comprise administering to a patient a therapeutically effective amount of a combination of (i) an anthracycline-loaded immunoliposome with a targeting moiety that is a first anti-HER2 antibody and (ii) an anti-cancer therapeutic comprising a second anti-HER2 antibody.

22 Claims, 16 Drawing Sheets

(56) References Cited

U.S. PATENT DOCUMENTS

| | | |
|---|---|---|
| 2010/0068255 A1 | 3/2010 | Benz et al. |
| 2010/0239652 A1 | 9/2010 | Rochlitz et al. |
| 2011/0059076 A1 | 3/2011 | McDonagh et al. |
| 2012/0231066 A1 | 9/2012 | Smith et al. |

FOREIGN PATENT DOCUMENTS

| | | |
|---|---|---|
| WO | 2009126920 A2 | 10/2009 |
| WO | 2010059315 A1 | 5/2010 |
| WO | 2012078695 A2 | 6/2012 |
| WO | 2014089127 A1 | 6/2014 |

OTHER PUBLICATIONS

Nielsen, Ulrik B., et al. "Therapeutic efficacy of anti-ErbB2 immunoliposomes targeted by a phage antibody selected for cellular endocytosis", Biochemica et Biophysica Acta, 1591 (2002), pp. 109-118.

"Assessing Surrogates of Clinical Cardiotoxicity Using Stem Cell-Derived Cardiiomyocytes" presented at Pharma/Bio Forum on Preclinical Development—Utilize Biomarkers and Leverage Partnerships for Earlier Toxicity Detection Conference, Sep. 26-27, 2011, Boston, Massachusetts (31 pages).

Gianni, Luca, et al. Anthracycline Cardiotoxicity in breast cancer patients: synergism with trastuzumab and taxanes, Cardiovasc Toxicol (2007) 7:67-71.

Cortes, Javier, Nonpegylated Liposomal Doxorubicin (TLC-D99), Paclitaxel, and Trastuzumab in HER-2-Overexpressing Breast Cancer: A Multicenter Phase I/II Study, Clin Cancer Res 2009;15(1), 2009, pp. 307-314 and Correction p. 1843 and cover page.

Kobrinsky, Boris, et al. "Documentation of Complete Response in Metastatic Breast Cancer to Liver and Bone Achieved with Trastuzumab and Pegylated Liposomal Doxorubicin," Clinical Medicine: Oncology 2008: 2 pp. 469-470.

Olson, Erin, "When Standard Therapy Fails in Breast Cancer: Current and Future Options for HER2-Positive Disease", J Clinical Trials, 2013, vol. 3, Issue 1, pp. 1-6.

Fuchs, Ilka B., et al. Analysis of HER2 and HER4 in Human Myocardium to Clarify the Cardiotoxicity of Trastuzumab (HerceptinTM), Breast Cancer Res Treat. 2003;82:23-28.

Hysing, J. et al. Cardiotoxic Effects of Trastuzumab, Tidsskr Nor Legeforen, Nov. 15, 2011;131(22), pp. 2239-2241.

International Search Report of PCT/US2013/072941, dated Mar. 25, 2014.

International Search Report of PCT/US2015/043867, dated Oct. 20, 2015.

Kirpotin, Dmitri B., et. al. Antibody Targeting of Long-Circulating Lipidic Nanoparticles Does Not Increase Tumor Localization but Does Increase Internalization in Animal Models, Cancer Res. 2006;66:6732-6740.

Lorusso, P., et al. "Assessment of safety and activity in an expanded phase 1 study of MM-302, a HER2-targeted liposomal doxorubicin, in patients with advanced HER2-positive (HER2+) breast cancer on behalf of the MM302 Phase I Team", (Feb. 14, 2014), XP055214984, Retrieved from the Internet: URL:http://tatcongress.org/wp-content/uploads/2014/05/140305-lorussso-mm302.pdf [retrieved on Sep. 21, 2015], pp. 6, 10, 12-15, and 21.

Nellis, David F., et al. Preclinical Manufacture of an Anti-HER2 scFv-PEG-DSPE, Liposome-Inserting Conjugate. 1. Gram-Scale Production and Purification, Biotechnol Prog., vol. 21 pp. 205-220 (2005).

Nellis et al. Preclinical Manufacture of Anti-HER2 Liposome-Inserting, scFv-PEG-Lipid Conjugate. 2. Conjugate Micelle Identity, Purity, Stability, and Potency AnalysisBiotecnol. Prog., 21:221-232 (2005).

Noble, Charles O., et al. Characterization of Highly Stable Liposomal and Immunolipsomal Formulations of Vincristine and Vinblastine, Cancer Chemother. Pharmacol. 2009 64:741-751.

Park, John W. et al. Anti-HER2 Immunoliposomes: Enhanced Efficacy Attributable to Targeted Delivery1, Clin Cancer Res. 2002;8:1172-1181.

Park, J.W., et al. "Tumor targeting using anti-HER2 immunoliposomes" Journal of Controlled Release, vol. 74: 95-113 (Dec. 31, 2001).

Sawyer, Douglas B., et al., "Mechanisms of Anthracycline Cardiac Injury: Can we identify strategies for cardio-protection?" Prog Cardiovasc Dis., Sep.-Oct. 2010;53(2):105-13.

Wickham, T.J., et al. "Preclinical safety and activity of MM-302, a HER2-targeted liposomal doxorubicin designed to have an improved safety and efficacy profile over approved anthracyclines." San Antonio Breast Cancer Symposium, Poster Presentation, 1 page, P3-14-09, Dec. 8, 2010.

Lazar, Greg A., et al. Engineered Antibody Fc Variants with Enhanced Effector Function, PNAS, vol. 13, No. 11 (2006), pp. 4005-4010.

Reynolds, J. G., et al. "HER2-targeted liposomal doxorubicin displays enhanced anti-tumorigenic effects without associated cardioxicity," Toxicology and Applied Pharmacology, 262 (2012), pp. 1-10.

Geretti, Elena, et al. "HER2-targeted liposomal doxorubicin, MM-302, has a favorable cardiosafety profile in preclinical models", American Association for Cancer Research (AACR) NCI-EORTC International Conference on Molecular Targets and Cancer Therapeutics, Nov. 12-16, 2011. (Poster #C90). Retrieved from the internet: URL:http://www.merrimack.com/files/MM-302/Preclinical%20Posters/AACR-EORTC%202011/AACR%20Mol%20Targets%202011%20MM-302%20EG%20final.pdf.

Geretti, Elena, et al. "Quantification of HER2 expression at the single cell level and HER2 intratumoral heterogeneity of breast cancer tissue samples using automated image analysis", San Antonio Breast Cancer Symposium, Dec. 4-8, 2012 (Poster # P1-07-03). Retrieved from the internet: URL: http://www.merrimack.com/files/MM-302/Preclinical%20Posters/San%20Antonio%20Breast%20Cancer%20Symposium%202012/2012-10-17-HER2-DX-approved.pdf.

Geretti, Elena, et al. "Tumor priming with cyclophosphamide increases delivery and activity of HER2-targeted liposomal doxorubicin (MM-302) in preclinical models of breast cancer", American Association for Cancer Research (AACR) Annual Meeting 2013 (Apr. 6-10, 2013) (Poster #3271). Retrieved from the internet: URL:http://www.merrimack.com/files/MM-302/Preclinical%20Posters/AACR%202013/AACR%202013%20Poster_MM302.pdf.

Hendriks, B. S., et al. "Impact of Tumor HER2/ERBB2 Expression Level on HER2-Targeted Liposomal Doxorubicin-Mediated Drug Delivery: Multiple Low-Affinity Interactions Lead to a Threshold Effect", Molecular Cancer Therapeutics, 12(9) Sep. 2013, pp. 1816-1828, 2962 and supplemental page. Published OnlineFirst May 30, 2013.

Hendriks, Bart, et al. "Physiologically-based PK modeling of liposomal drug delivery points to a key role of tumor deposition in determining the relative efficacy of liposomal vs. free doxorubicin in breast cancer and Kaposi sarcoma", 102nd American Association for Cancer Research (AACR) Annual Meeting 2011, Apr. 2-6, 2011. Retrieved from the internet: URL: http://cancerres.aacrjournals.org/content/71/8_Supplement/4915.abstract.

Klinz, Stephan, et al. "MM-302, a HER2-targeted liposomal doxorubicin, shows binding/uptake and efficacy in HER2 2+ cells and xenograft models", 102nd American Association for Cancer Research (AACR) Annual Meeting 2011, Apr. 2-6, 2011 (Poster #3637). Retrieved from the internet: URL:http://www.merrimack.com/files/MM-302/Preclinical%20Posters/AACR%202011/10.%20AACR%202011%20MM-302%20HER2%20Threshold%20Klintz.pdf.

Reynolds, Joe, et al. "MM-302, HER2-targeted liposomal doxorubicin, does not impair cardiomyocyte function in vitro", 102nd American Association for Cancer Research (AACR) Annual Meeting 2011, Apr. 2-6, 2011 (Poster #3638). Retrieved from the internet: URL: http://www.merrimack.com/files/MM-302/Preclinical%20Posters/AACR%202011/AACR2011%20MM-302%20Cardiomyocyte%20JReynolds.pdf.

(56) References Cited

OTHER PUBLICATIONS

Clinical Trials Archive: "A Phase 1, Multi-Center, Open-Label, Dose-Escalation, Safety, and Pharmacokinetic Clinical Study of Intravenously Administered MM-302 Monotherapy and in Combination with Trastuzumab with or without Cyclophosphamide in Patients with Advanced HER2 Positive Breast Cancer" Nov. 17, 2011, pp. 1-3, XP055273289, Retrieved from the Internet: URL:https://clinicaltrials.gov/archive/NCT01304797/2011_11_17 *the whole document*.

Doxorubicin Hydrochloride for Injection, USP Packaging Label, Pfizer, Inc., Revised May 2010, pp. 1-22.

EPAR Summary for Caelyx, European Medicines Agency (2010) and Annex I—Summary of Product Characteristics, 46 pages.

EPAR Summary for Myocet, European Medicines Agency (2013) and Annex I—Summary of Product Characteristics, 37 pages.

Extended European Search Report with Supplementary European Search Report, and European Search Opinion for EP 13 86 0427, issued May 30, 2016.

Harrington, Kevin J., et al. "Effective Targeting of Solid Tumors in Patients with Locally Advanced Cancers by Radiolabeled Pegylated Liposomes", Clinical Cancer Research, vol. 7, pp. 243-254 (2001).

Mamot, Christoph, et al. "Liposome-based approaches to overcome anticancer drug resistance", Drug Resistance Updates 6 (2003), pp. 271-279.

Martin, M., et al. "Pegylated liposomal doxorubicin in combination with cyclophosphamide and trastuzumab in HER2-positive metastatic breast cancer patients: efficacy and cardiac safety from the GEICAM/2004/05 study", Annals of Oncology., vol. 22, No. 12, Mar. 17, 2011, pp. 2591-2596.

Mufamadi, Maluta, S., et al. "A Review on Composite Liposomal Technologies for Specialized Drug Delivery", Journal of Drug Delivery, vol. 2011, Article ID 939851, 19 pages.

O'Brien, M.E.R., et al. Reduced cardiotoxicity and comparable efficacy in a phase III trial of pegylated liposomal doxorubicin HCI (CAELYXTM/Doxil®) versus conventional doxorubicin for first-line treatment of metastatic breast cancer, Annals of Oncology 15:440-449 (2004).

Rayson, D., et al. "Cardiac safety of adjuvant pegylated liposomal doxorubicin with concurrent trastuzumab: a randomized phase II trial", Annals of Oncology., vol. 23, No. 7, Nov. 4, 2011, pp. 1780-1788.

Reynolds, J., et al. "MM-302, a Her2-Targeted Liposomal Doxorubicin, Limits Doxorubicin Accumulation in Cardiomyocytes, and Enhances Doxorubicin Uptake into Tumor Cells in Vitro" Society of Toxicology, 50th Annual Meeting and ToxExpo, Washington, D.C., ISSN: 1096-6080, vol. 120, Suppl. 2, Mar. 6-10, 2011 (Abstract 1888).

Shmeeda, H., et al. "Her2-targeted pegylated 1-15 liposomal doxorubicin: Retention of target-specific binding and cytotoxicity after in vivo passage", Journal of Controlled Release, Elsevier, Amsterdam, NL, vol. 136, No. 2, Jun. 5, 2009, pp. 155-160, XP026108534, ISSN: 168-3659, DOI 10.1016/J.JCONREL.2009.02.02 [retrieved on Feb. 7, 2009] *paragraph [discussion]*.

Siwak, D., et al. Commentary re: J. W. Park et al., The potential of drug-carrying immunoliposomes as anticancer agents, Clinical Cancer Research 8 (2002) pp. 955-956.

Stickeler, Elmar, et al. "Pegylated liposomal doxorubicin and trastuzumab as 1st and 2nd line therapy in her2/neu positive metastatic breast cancer: a multicenter phase II trial", Breast Cancer Research and Treatment, Kluwer Academic Publishers, BO, vol. 117, No. 3, Jan. 21, 2009, pp. 591-598.

Wolff, Antonio, et al. "Phase II trial of pegylated liposomal doxorubicin plus docetaxel with and without trastuzumab in metastatic breast cancer: trastuzumab in metastatic breast cancer: Eastern Cooperative Oncology Group Trial E3198", Breast Cancer Research and Treatment, Kluwer Academic Publishers, BO, vol. 121, No. 1, Mar. 24, 2010, pp. 111-120.

Bauwens, Celine L., et al., "Geometric Control of Cardiomyogenic Induction in Human Pluripotent Stem Cells" Tissue Eng Part A. Aug. 2011, vol. 17, No. 15-16:1901-1909 PMID 21417693.

Clinical Trials Archive: "A Phase 1, Multi-Center, Open-Label, Dose-Escalation, Safety, and Pharmacokinetic Clinical Study of Intravenously Administered MM-302 Monotherapy and in Combination with Trastuzumab with or without Cyclophosphamide in Patients with Advanced HER2 Positive Breast Cancer" (Feb. 26, 2014), pp. 1-4, XP055214989, Retrived from the Internet URL:https://clinicaltrials.gov/archive/NCT01304797/2014_02_26 [retrieved on Sep. 21, 2015] the whole document.

Corresponding Chinese Patent Application No. 201180066002.5— English Translation of Notification of the Second Office Action and Search Report, dated May 11, 2015.

Doxil® Prescribing Information, Ortho Biotech Products, LP, Raritan, NJ, May 2007.

Ewer, Michael S., et al. "Cardiac Safety of Liposomal Anthracyclines." Elsevier, Seminars in Oncology (2004), pp. 161-181.

Exhibit A (Eqivalent Surface Area Dosage Conversion Factors, 2015).

* cited by examiner

COMBINATION THERAPY FOR TREATING HER2-POSITIVE CANCERS

CROSS-REFERENCE TO RELATED APPLICATIONS

This application is a U.S. National Phase of PCT/US2013/072941, filed Dec. 3, 2013, which claims the benefit of and priority to U.S. Provisional Patent Application No. 61/732,736, filed Dec. 3, 2012, and 61/810,254, filed Apr. 9, 2013. The entire contents of each of the foregoing applications are incorporated herein by reference in their entirety.

BACKGROUND

Over-expression of Human Epidermal Growth Factor Receptor 2 (HER2)—also known as NEU, ERBB-2, CD340, or p185—is associated with a variety of cancers including, e.g., breast cancer, ovarian cancer, stomach cancer, uterine cancer, melanoma, and cholangiocarcinoma. For example, HER2 over-expression is typically associated with aggressive, metastatic forms of breast cancer that have high rates of recurrence and/or are associated with poor patient prognosis.

Anthracyclines have been used as effective cancer therapies for decades, and anthracycline-based regimens have demonstrated clinical benefit for treating breast cancer. Unfortunately, such anthracycline-based regimens are associated with significant toxicities such as, for example, acute and/or chronic cardiac dysfunction, which have limited their therapeutic use. In an effort to improve the safety and efficacy of currently available anthracyclines, immunoliposomal formulations have been prepared that contain the anthracycline doxorubicin in liposomes having antibodies in their exterior surfaces that target HER2 overexpressing cancer cells and do not block (e.g., the antibodies do not block) HER2-mediated signaling.

Another approach to treating HER2 overexpressing cancers has focused on the use of anti-HER2 antibodies that inhibit HER2 signaling. For example, trastuzumab (HERCEPTIN®) is a therapeutic anti-HER2 antibody that blocks intracellular signaling mediated by HER2 and is widely used to treat HER2 overexpressing tumors. Unfortunately, a key dosage-limiting effect of trastuzumab is cardiotoxicity. Cardiomyocytes are known to express HER2, and trastuzumab-mediated cardiotoxicity is generally believed to result from damage to HER2-expressing cardiomyocytes that results from trastuzumab binding to the cardiomyocyte-expressed HER2. As both anthracycline drugs and anti-HER2 antibodies are associated with related serious side effects (i.e., cardiotoxicity), there remains a critical need to optimize established therapies and develop new, therapies that will provide better anti-cancer effects with fewer adverse effects on the heart and thereby prolong patients' lives with reduced negative impacts on quality of life.

SUMMARY

Provided herein are compositions and methods for treating HER2 positive cancer in a human patient, the methods comprising co-administering to the patient 1) a preparation of HER2-targeted, anthracycline-loaded immunoliposomes (immunoliposomes comprising an encapsulated anthracycline and a first anti-HER2 antibody, also referred to herein as anthracycline-loaded anti-HER2 immunoliposomes) and 2) an anti-cancer therapeutic comprising a second anti-HER2 antibody. The combination is co-administered (or is for co-administration), e.g., according to a clinical dosage regimen disclosed herein (particular dose amounts given according to a specific dosing schedule).

In one embodiment, the first anti-HER2 antibody does not compete with the second anti-HER2 antibody for binding to HER2.

In various embodiments: The first anti-HER2 antibody is not an inhibitor of HER2 signaling; the second anti-HER2 antibody is an inhibitor of HER2 signaling; the compositions are for administration in, and the method comprises, at least one treatment cycle, wherein the cycle is a period of 4 weeks, and wherein for each cycle the second anti-HER2 antibody is administered at a weekly dose of 6 mg/kg and the anthracycline-loaded anti-HER2 immunoliposome preparation is administered once every 4 weeks at a dose of 30 mg/m$^2$ total anthracycline.

In yet another embodiment, the therapeutically effective amount includes administering the anthracycline-loaded anti-HER2 immunoliposome as a monotherapy prior to said at least one cycle. In another embodiment, the anthracycline-loaded anti-HER2 immunoliposome monotherapy is administered every three weeks, wherein the second anti-HER2 antibody is administered at 6 mg/kg the first week and at 4 mg/kg the second and third weeks.

In various embodiments, the HER2-positive cancer is breast cancer. The HER2-positive breast cancer may test positive for estrogen receptor and may be a HER2 non-amplified invasive breast cancer. The HER2-positive breast cancer may be advanced. The breast cancer may be metastatic. The HER2-positive breast cancer may be advanced/metastatic breast cancer.

In other embodiments, the cancer is selected from the group consisting of bladder cancer, breast cancer, sarcoma, endometrial cancer, esophageal cancer, gastric cancer, gastro-esophageal junction cancer, ovarian cancer, lung cancer, colorectal cancer pancreatic cancer, and multiple myeloma.

In certain embodiments, the second anti-HER2 antibody is administered prior to administration of the anthracycline-loaded anti-HER2 immunoliposome.

In other embodiments, the anthracycline-loaded anti-HER2 immunoliposome is administered by a route selected from the group consisting of intravenous, intrathecal, intravesicular, intraperitoneal, and intramuscular.

In various embodiments, the second anti-HER2 antibody is an anti-HER2 monoclonal antibody, an anti-HER2 oligoclonal antibody, or an anti-HER2 polyclonal antibody. In further embodiments, the second anti-HER2 antibody is trastuzumab. In yet further embodiments, the second anti-HER2 antibody is ado-trastuzumab emtansine.

In other embodiments, the anthracycline is doxorubicin. In other embodiments, the anthracycline-loaded anti-HER2 immunoliposome is MM-302.

In still other embodiments, the HER2-expressing cancer is further characterized as being HER2$^{1+}$, HER2$^{2+}$, HER2$^{3+}$ (e.g., via the HERCEPTEST assay or another such semi-quantitative immunohistochemical assay using a polyclonal anti-HER2 primary antibody), or is HER2-positive, FISH-negative (fluorescent in-situ hybridization-negative).

In other embodiments, the anthracycline-loaded anti-HER2 immunoliposome is administered at a dosage lower than is recommended for monotherapy administration of the anthracycline.

In yet another embodiment, during combination therapy the second anti-HER2 antibody is administered at a dosage lower than would be used when the second anti-HER2 antibody is administered as monotherapy. In certain embodiments, the immunoliposome is administered so as to deliver a higher accumulated dose of the anthracycline than is recommended for monotherapy administration of the anthracycline.

In another aspect, the techniques herein provide compositions for and a methods of treatment of HER2-positive breast cancer in a human patient, the method including co-administering to the patient a therapeutically effective amount of MM-302 and a therapeutically effective amount of trastuzumab.

In another aspect, techniques disclosed herein provide a method for use in treating a HER2-positive cancer in a human patient including a safe and effective amount of an immunoliposome comprising an encapsulated anthracycline and a first anti-HER2 antibody, and a safe and effective amount of a second anti-HER2 antibody.

In another embodiment, a method is provided for treating a HER2-positive breast cancer in a human patient, the method comprising: determining a safe and effective dosage for an anthracycline-loaded anti-HER2 immunoliposome for the patient; administering the immunoliposome to the patient at the safe and effective dosage for the immunoliposome; determining a safe and effective dosage for an anti-HER2 antibody for the patient; and administering the antibody to the patient at the safe and effective dosage for the antibody; where the immunoliposome and the anti-HER2 antibody are co-administered.

In various embodiments, the immunoliposome is MM-302.

In other embodiments, the second anti-HER2 antibody is formulated for intravenous administration at a dose of 2 mg/kg, 4 mg/kg, 6 mg/kg, 8 mg/kg, or 10 mg/kg.

In another embodiment, the co-administration does not cause cardiotoxicity to the patient to any greater extent than does monotherapy administration of the second anti-HER2 antibody.

In another aspect, the invention provides method of treatment of a HER2-positive cancer in an anthracycline naïve human patient, the method comprising co-administering to the patient a therapeutically effective amount of each of (i) an immunoliposome comprising an encapsulated anthracycline and a targeting moiety that is a first anti-HER2 antibody and (ii) an anti-cancer therapeutic comprising a second anti-HER2 antibody.

In certain embodiments, the treatment does not result in a reduction of left ventricular ejection fraction (LVEF) of greater than 10% in more than 0.5% or more than 1%, or more than 2% of treated patients. In certain embodiments, the reduction of left ventricular ejection fraction LVEF is not greater than 5%. In certain embodiments, the second anti-HER2 antibody is trastuzumab.

In another aspect, a kit is provided comprising a first container comprising: i) a second container containing a preparation of an anti-HER2 immunoliposome comprising an encapsulated anthracycline and a first anti-HER2 antibody; and ii) instructions for co-administration of the immunoliposome with a second anti-HER2 antibody according to the above-described aspects and embodiments. In certain embodiments, the first container further comprises at least one dose of the second anti-HER2 antibody.

DETAILED DESCRIPTION

Figure 1A:
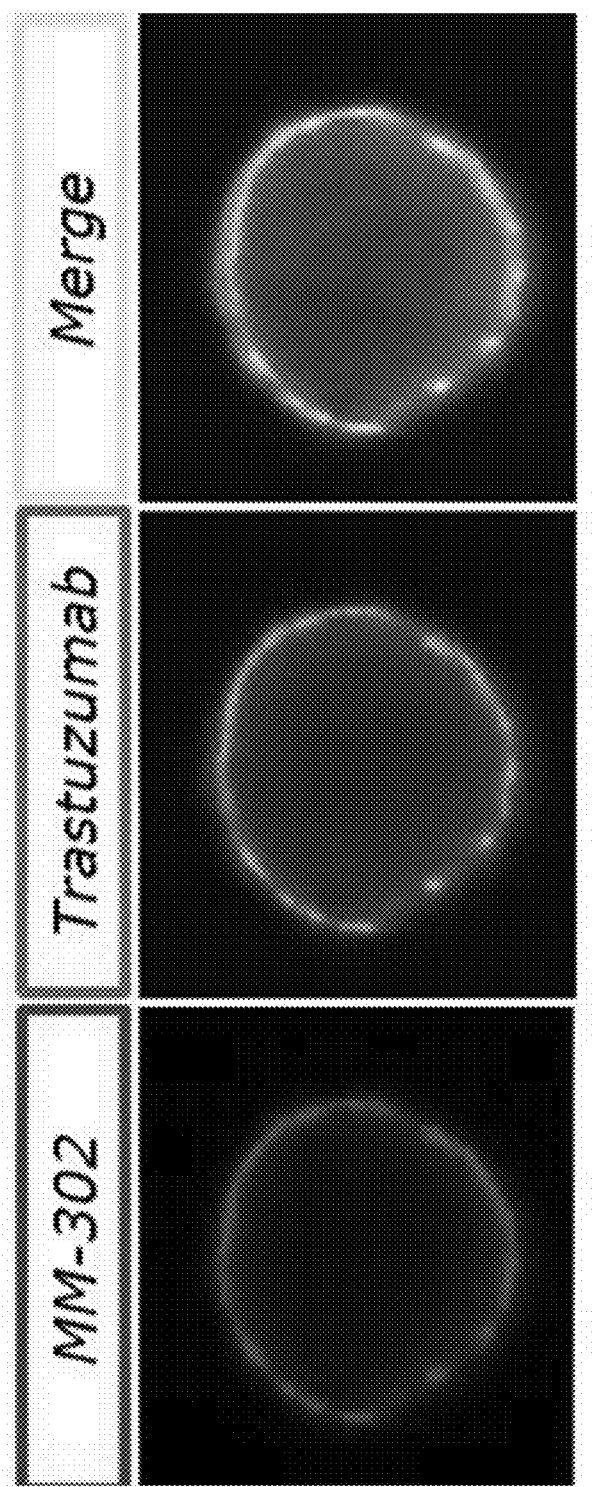
FIG. 1A is three images showing confocal microscopy of a BT-474 cell co-incubated with 1 μM fluorescently labeled MM-302 (DIi5-fluorphore; left panel) and 1 μM trastuzumab (488-fluorophore; middle panel) show that both agents co-localize to the cell membrane (right panel).

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

By "ameliorate" is meant decrease, suppress, attenuate, diminish, arrest, or stabilize the development or progression of a disease.

The term "antibody" includes antibodies and antibody variants comprising at least one antibody derived antigen binding site (e.g., VH/VL region or Fv) that specifically binds to HER2. Antibodies include known forms of antibodies. For example, the antibody may be a human antibody, a humanized antibody, a bispecific antibody, or a chimeric antibody. The antibody may also be a Fab, Fab'2, ScFv, SMIP, Affibody®, nanobody, or a domain antibody. The antibody may also be any of the following isotypes: IgG1, IgG2, IgG3, IgG4, IgM, IgA1, IgA2, IgAsec, IgD, and IgE.

As used herein, the term "antibody variant" includes naturally occurring antibodies which have been altered (e.g., by mutation, deletion, substitution, conjugation to a nonantibody moiety) to include at least one variant amino acid which changes a property of the antibody. For example, numerous such alterations are known in the art which affect, e.g., half-life, effector function, and/or immune responses to the antibody in a patient. The term antibody variant also includes artificial polypeptide constructs which comprise at least one antibody-derived binding site.

By "anthracyclines" is meant a class of drugs structurally related to and including daunorubicin, which is derived from *Streptomyces peucetius* var. *caesius*, which are used in cancer chemotherapy. Exemplary anthracyclines include, but are not limited to, daunorubicin, doxorubicin, epirubicin, idarubicin, and valrubicin. As used herein, "cancer" refers to a condition characterized by abnormal, unregulated, malignant cell growth. In some embodiments, the cancer tumor is a HER2⁺ solid tumor type, e.g., a melanoma, a cholangiocarcinoma, clear cell sarcoma, or an esophageal, head and neck, endometrial, prostate, breast, ovarian, gastric, gastroesophageal junction (GEJ), colon, colorectal, lung, bladder, pancreatic, salivary gland, liver, skin, brain or renal tumor. In other embodiments, the cancer is squamous cell cancer, small-cell lung cancer, non-small cell lung cancer, cervical cancer, or thyroid cancer.

By "co-administration" is meant concurrent or sequential administration of two different therapeutic agents (a first therapeutic agent and a second therapeutic agent) where both administrations are administered close enough in time to each other that the first and second therapeutic agents are simultaneously present in patients receiving the co-administration.

By "disease" is meant any condition or disorder that damages or interferes with the normal function of a cell, tissue, or organ.

The term "doxorubicin" refers to the drug with the chemical name (8S,10S)-10-(4-amino-5 hydroxy-6-methyltetrahydro-2H-pyran-2-yloxy)-6,8,11-trihydroxy-8-(2-hydroxyacetyl)-1-methoxy-7,8,9,10-tetrahydrotetracene-5,12-dione. It is marketed under the trade names Adriamycin PFS®, Adriamycin RDF®, or Rubex®. Doxorubicin is an anthracycline antibiotic, closely related to the natural product daunomycin, and like all anthracyclines, it is believed to work by intercalating DNA. Typically, the drug is administered intravenously, e.g., in the form of hydrochloride salt. Doxorubicin is photosensitive, and containers comprising it are often covered by an aluminum bag and/or brown wax paper to prevent light from affecting it.

By "MM-302" is meant a unilamellar lipid bilayer vesicle of approximately 75-110 nm in diameter that encapsulates an inner aqueous space which contains doxorubicin in a gelated or precipitated state. The lipid membrane is composed of phosphatidylcholine, cholesterol, and a polyethyleneglycol-derivatized phosphatidylethanolamine in the amount of approximately one PEG molecule for 200 phospholipid molecules, of which approximately one PEG chain for each 1780 phospholipid molecules bears at its end an F5 single-chain Fv antibody fragment that is exposed on the outer surface of the vesicle and binds to HER2. MM-302 is described (together with methods of making and using MM-302) in, e.g., co-pending PCT Patent Publication No. WO 2012/078695 (U.S. patent application Ser. No. 13/912, 167, filed Jun. 6, 2013), the contents of which are incorporated herein by reference in their entirety.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reference" is meant a standard or control condition. In one embodiment, the effect of an agent on a cell is compared to the effect of the agent on a control cell.

As used herein, the term "subject" or "patient" refers to a human cancer patient.

"Therapeutic agent" means a substance that has the potential of affecting the function of an organism. Such a substance may be, for example, a naturally occurring, semisynthetic, or synthetic agent or a biological molecule such as an antibody, or a complex assemblage such as a liposome or an immunoliposome. For example, an agent may be a drug that targets a specific function of an organism or an antibiotic. A therapeutic agent may decrease, suppress, attenuate, diminish, arrest, or stabilize the development or progression of disease, disorder, or infection in a eukaryotic host organism.

The term "therapeutically effective amount" refers to an amount of an agent that provides the desired biological, therapeutic, and/or prophylactic result. That result may be reduction, amelioration, palliation, lessening, delaying, and/or alleviation of one or more of the signs, symptoms, or causes of a disease, or any other desired alteration of a biological system. In reference to cancers (e.g., HER2 overexpressing cancers), a therapeutically effective amount comprises an amount sufficient to cause a tumor to shrink and/or to decrease the growth rate of the tumor (such as to suppress tumor growth), or to prevent or delay other unwanted cell proliferation. In some embodiments, a therapeutically effective amount is an amount sufficient to delay tumor development. In some embodiments, a therapeutically effective amount is an amount sufficient to prevent or delay tumor recurrence. A therapeutically effective amount may be administered in one or more administrations. The therapeutically effective amount of a drug or composition may: (i) reduce the number of cancer cells; (ii) reduce tumor size; (iii) inhibit, retard, slow to some extent, and/or stop cancer cell infiltration into peripheral organs; (iv) inhibit (i.e., slow to some extent and may stop) tumor metastasis; (v) inhibit tumor growth; (vi) prevent or delay occurrence and/or recurrence of tumor; and/or (vii) relieve to some extent one or more of the symptoms associated with the cancer. In one example, a "therapeutically effective amount" is the amount required to provide a clinically significant decrease in breast cancer or slowing of progression of breast cancer.

Compositions and methods are provided that are effective for treating patients with histologically or cytologically confirmed advanced cancer that is positive for HER2 (HER2$^+$). HER2$^+$ cancers are those in which the tumor cells overexpress HER2. A tumor that overexpresses HER2 is one that is identified as being HER2 "3+" or HER2 "2+" by immunohistochemistry (e.g., by HercepTest®), or gene-amplified positive by fluorescence in situ hybridization (FISH+). In some embodiments, a tumor may be Her2$^+$ as determined by immunohistochemistry but negative for Her2 as determined by FISH. Chromogenic in situ hybridization (CISH) may also be used if FISH results are unavailable. Patients can be tested or selected for one or more of the above described clinical attributes prior to, during or after treatment.

As used herein, "cancer" refers to a condition characterized by abnormal, unregulated, malignant cell growth. In some embodiments, the cancer tumor is a HER2+ solid tumor type, e.g., a melanoma, a cholangiocarcinoma, clear cell sarcoma, or an esophageal, head and neck, endometrial, prostate, breast, ovarian, gastric, gastro-esophageal junction (GEJ), colon, colorectal, lung, bladder, pancreatic, salivary gland, liver, skin, brain or renal tumor. In other embodiments, the cancer is squamous cell cancer, small-cell lung cancer, non-small cell lung cancer, cervical cancer, or thyroid cancer.

In one embodiment, the invention provides compositions comprising MM-302 for use in combination with an anti-HER2 antibody, and methods of using the composition for the treatment of breast cancer. In other embodiments, the invention provides compositions comprising MM-302 administered in combination with trastuzumab, wherein the combination is administered (or is for administration) according to a particular clinical dosage regimen (i.e., at a particular dose amount and according to a specific dosing schedule).

It has surprisingly been discovered that concurrent or sequential co-administration of a HER2-targeted anthracycline-loaded immunoliposome (e.g., MM-302) and an anti-HER2 antibody (e.g., trastuzumab), results in the efficacious treatment of breast cancer without an increased risk of cardiotoxicity.

MM-302 Liposomes

"MM-302" refers to a HER2-targeted immunoliposome comprising an anthracycline anti-cancer therapeutic. Immunoliposomes are antibody (typically antibody fragment) targeted liposomes that provide advantages over non-immunoliposomal preparations because they are selectively internalized by cells bearing cell surface antigens targeted by the antibody. Such antibodies and immunoliposomes are described, for example, in the following US patents and patent applications: U.S. Pat. Nos. 7,871,620, 6,214,388, 7,135,177, and 7,507,407 ("Immunoliposomes that optimize internalization into target cells"); U.S. Pat. No. 6,210,707 ("Methods of forming protein-linked lipidic microparticles and compositions thereof"); U.S. Pat. No. 7,022,336 ("Methods for attaching protein to lipidic microparticles with high efficiency"); and U.S. Pat. Nos. 7,892,554 and 7,244,826 ("Internalizing ErbB2 antibodies."). Immunoliposomes targeting HER2 can be prepared in accordance with the foregoing patent disclosures. Such HER2 targeted immunoliposomes include MM-302, which comprises the F5 anti-HER2 antibody fragment and contains doxorubicin. MM-302 contains an average of 45 copies of mammalian-derived F5-scFv (anti-HER2) per liposome.

An MM-302 liposome is a unilamellar lipid bilayer vesicle of approximately 75-110 nm in diameter that encapsulates an aqueous space that contains doxorubicin. The lipid membrane is composed of phosphatidylcholine, cholesterol, and a polyethyleneglycol-derivatized phosphatidylethanolamine in the amount of approximately one PEG molecule for 200 phospholipid molecules, of which approximately one PEG chain for each 1780 phospholipid molecules bears at its end an F5 single-chain Fv antibody fragment that binds immunospecifically to HER2.

Preferred tumors for treatment with MM-302 are those in which the tumor cells overexpress HER2. A tumor that overexpresses HER2 is one that is identified as being HER2$^{3+}$ or HER2$^2$HercepTest™, or HER2 FISH+ by fluorescence in situ hybridization. In some embodiments, MM-302 may be administered to a patient having a tumor that is HER2$^{1+}$ but which is also FISH+. Alternatively, MM-302 may be administered to a patient having a tumor that is FISH negative but is scored as HER2$^{3+}$ or HER2$^{2+}$ by IHC. Alternatively, a preferred tumor that overexpresses HER2 is one that expresses an average of 200,000 or more receptors per cell, as quantified by the methods described in the Examples.

In certain embodiments, MM-302 is administered as a monotherapy in the doses set forth in Table 1, above. In Table 1, "mg/m$^2$" indicates mg of doxorubicin (formulated as MM-302) per square meter of body surface area of the patient. For MM-302, the dosing regimens indicated with an * are preferred. Dosing regimens may vary in patients with solid tumors that are "early" (pre-metastatic, e.g., adjuvant breast cancer) as compared to "advanced" (metastatic tumors). In certain embodiments, MM-302 is administered as a monotherapy to a patient that has not previously been treated with an anthracycline therapeutic (an "anthracycline naïve" patient).

TABLE 1

MM-302 Monotherapy Dosing

| | Dose 1 | Dose 2 | Dose 3 | Dose 4 | Dose 5 | Dose 6 | Dose 7 | Dose 8 | Dose 9 |
|---|---|---|---|---|---|---|---|---|---|
| Every week | 10 mg/m$^2$ | 15 mg/m$^2$ | | | | | | | |
| Every two weeks | 10 mg/m$^2$ | 15 mg/m$^2$ | 20 mg/m$^2$ | 25 mg/m$^2$ | | | | | |
| Every three weeks | | 15 mg/m$^2$ | 20 mg/m$^2$ | 25 mg/m$^2$ | 30 mg/m$^2$ | 35 mg/m$^2$ | 40 mg/m$^2$ | | |
| Every four weeks | | | 20 mg/m$^2$ | 25 mg/m$^2$ | 30 mg/m$^2$ | 35 mg/m$^2$ | 40 mg/m$^2$ | 45 mg/m$^2$ | 50 mg/m$^2$ |
| Every five weeks | | | | | 30 mg/m$^2$ | 35 mg/m$^2$ | 40 mg/m$^2$ | 45 mg/m$^2$ | 50 mg/m$^2$ |

TABLE 2

MM-302 and trastuzumab dosing

| | Dose 1 | Dose 2 | Dose 3 | Dose 4 | Dose 5 | Dose 6 | Dose 7 | Dose 8 | Dose 9 |
|---|---|---|---|---|---|---|---|---|---|
| Every week[a] | 10 mg/m$^2$ | 15 mg/m$^2$ | | | | | | | |
| Every two weeks[b] | 10 mg/m$^2$ | 15 mg/m$^2$ | 20 mg/m$^2$ | 25 mg/m$^2$ | | | | | |
| Every three weeks[c] | | 15 mg/m$^2$ | 20 mg/m$^2$ | 25 mg/m$^2$ | 30 mg/m$^2$ | 35 mg/m$^2$ | 40 mg/m$^2$ | | |
| Every four weeks | | | 20 mg/m$^2$ | 25 mg/m$^2$ | 30 mg/m$^2$ | 35 mg/m$^2$ | 40 mg/m$^2$ | 45 mg/m$^2$ | 50 mg/m$^2$ |
| Every five weeks | | | | | 30 mg/m$^2$ | 35 mg/m$^2$ | 40 mg/m$^2$ | 45 mg/m$^2$ | 50 mg/m$^2$ |

[a] trastuzumab will be administered weekly at 2 mg/kg (4 mg/kg loading dose)
[b] trastuzumab will be administered every two weeks at 4 mg/kg (6 mg/kg loading dose)
[c] trastuzumab will be administered every three weeks at 6 mg/kg (8 mg/kg loading dose)

In certain embodiments, MM-302 is administered in combination with trastuzumab in the doses set forth in Table 2, above. In other embodiments, MM-302 is administered in combination with another HER2-targeted monoclonal antibody, e.g., pertuzumab, TDM-1 or MM-111.

Dosage and Administration of MM-302

MM-302 may be administered by IV infusion over 60 minutes on the first day of each 1-, 2-, 3-, 4-, or 5-week cycle. The first cycle Day 1 is a fixed day. Subsequent doses may be administered on the first day of each cycle±3 days. Prior to administration, the appropriate dose of MM-302 must be diluted in 5% Dextrose Injection, USP. Care should be taken not to use in-line filters or any bacteriostatic agents such as benzyl alcohol.

MM-302 may be administered at a dose that ranges from about 100 mg/m$^2$ to about 1 mg/m$^2$. In other embodiments, MM-302 may be administered at a dose that ranges from about 50 mg/m$^2$ to about 2 mg/m$^2$. In other embodiments, MM-302 may be administered at a dose that ranges from about 40 mg/m$^2$ to about 3.22 mg/m$^2$. In still other embodiments, MM-302 may be administered at a dose of 60 mg/m$^2$, 55 mg/m$^2$, 50 mg/m$^2$, 45 mg/m$^2$, 40 mg/m$^2$, 35 mg/m$^2$, 30 mg/m$^2$, 25 mg/m$^2$, 20 mg/m$^2$, 16 mg/m$^2$, 14 mg/m$^2$, 12 mg/m$^2$, 10 mg/m$^2$, 8 mg/m$^2$, 6 mg/m$^2$, 4 mg/m$^2$, and/or 3.2 mg/m$^2$. In another embodiment, MM-302 may be administered at a dose of 50 mg/m$^2$, 40 mg/m$^2$, 30 mg/m$^2$, 16 mg/m$^2$, or 8 mg/m$^2$.

Pretreatment with or concomitant use of anti-emetics may be considered according to institutional guidelines. The actual dose of MM-302 to be administered is determined by calculating the patient's body surface area at the beginning of each cycle. A ±5% variance in the calculated total dose can be permitted for ease of dose administration.

Dose Modification for Cardiac Systolic Dysfunction

Cardiac function should be monitored during treatment. If left ventricular ejection fraction (LVEF) drops greater than 10 absolute percentage points from baseline and remains below or equal to 50%, dosing with MM-302 should be withheld, unless the benefits for the individual patient are deemed to outweigh the risks and following documented discussion with the Medical Monitor. If MM-302 is re-administered, repeat echocardiogram (ECHO) or multi gated acquisition radionuclide angiography (MUGA) must be performed prior to each additional dose. If repeat MUGA or ECHO demonstrates either further decline in LVEF of >10 absolute percentage points or an ejection fraction of less than 50%, the patient will permanently discontinue MM-302 therapy.

Patients who experience decline in LVEF by >5 but <10 absolute percentage points from baseline to a final value that is <50% may remain on MM-302 treatment if they are experiencing clinical benefit, at the discretion of the medical monitor. If MM-302 is re-administered, repeat ECHO or MUGA should be performed prior to each additional dose. If repeat MUGA or ECHO demonstrates further decline in LVEF, the patient should permanently discontinue MM-302 therapy.

If LVEF drops 10 absolute percentage points or greater from baseline and to below 50% in patients with a normal baseline measurement, MM-302 should be withheld and a repeat LVEF assessment performed within approximately 3 weeks. If LVEF has not improved, or declined further, MM-302 should be discontinued. If MM-302 is re-administered, repeat ECHO or MUGA should be performed prior to each additional dose. If repeat MUGA or ECHO demonstrates further decline in LVEF, the patient should permanently discontinue MM-302 therapy.

If the benefits for the individual patient are deemed to outweigh the risks of asymptomatic changes in LVEF, treatment with MM-302 may be continued.

If symptomatic cardiac failure develops (NYHA Class III or IV) during treatment, MM-302 should be discontinued.

Doses, Preparation and Administration of Trastuzumab

Preparation of trastuzumab should be followed as stated in the package insert. In one embodiment, the initial weekly dose of trastuzumab may range from about 50 mg/kg to about 2 mg/kg. For example, in one embodiment the initial weekly dose of trastuzumab is 4 mg/kg as a 90 minute infusion followed by subsequent weekly doses of 2 mg/kg as 30 minute IV infusions that will be administered to patients in the combination cohort. The initial Q3 weekly dose of 8 mg/kg over 90 minute IV infusion followed by 6 mg/kg over 30 to 90 minutes IV infusion will be administered to patients in the final cohort.

Management of Toxicities Related to Trastuzumab

Dose reductions that are felt to be related and/or significant by the Investigator should be managed per the package insert. If cardiac toxicity occurs when MM-302 and trastuzumab are being given in combination, trastuzumab should be concurrently held or discontinued as outlined for MM-302 herein.

MM-302 Monotherapy of Advanced Breast Cancer

MM-302 may be administered once every 4 weeks by intravenous (IV) infusion over 60 minutes at 8, 16, 30, 40, or 50 mg/m$^2$ to patients with locally advanced/unresectable or metastatic advanced breast cancer that overexpresses HER2 as determined by FISH or by IHC or by determination of the average number of HER2 receptors per cell. Patients should have adequate bone marrow reserves as evidenced by: 1) absolute neutrophil count (ANC) ≥1,500/μL; 2) platelet count ≥100,000/μL and 3) hemoglobin ≥9 μg/dL (Transfusions allowed). Patients should have adequate hepatic function as evidenced by: 1) serum total bilirubin ≤1.5×ULN and 2) Aspartate aminotransferase (AST), Alanine aminotransferase (ALT) and Alkaline Phosphatase (ALP) normal or up to 2.5× upper limit of normal (ULN; 5×ULN is acceptable for ALP if liver metastases and/or bone metastases are present). Patients should have adequate renal function as evidenced by a serum creatinine ≤1.5×ULN. Patients should be recovered from any clinically relevant toxic effects of any prior surgery, radiotherapy or other therapy intended for the treatment of breast cancer. Women of childbearing potential as well as fertile men and their partners must be warned to abstain from sexual intercourse or to use an effective form of contraception during treatment and for 90 days following the last dose of MM-302. Patients should have adequate cardiac function as evidenced by a measured left ventricular ejection fraction of ≥50% by ECHO or MUGA within approximately 30 days of treatment. Patients who are pregnant or lactating and those with NYHA Class III or IV congestive heart failure or left ventricular ejection fraction (LVEF) <50%, or a prolonged QTc interval (≥460 ms), are preferably not be treated with MM-302.

MM-302 In Vitro Pharmacology

In vitro pre-clinical pharmacology studies of MM-302 have demonstrated that MM-302 cross-reacts with cynomolgus HER2 but not with rat HER2. Additionally, the number of HER2 receptors needed per cell to optimize the binding of MM-302 is approximately 200,000 HER2 receptors per cell. Below this level, binding is low and comparable with untargeted pegylated liposomal doxorubicin. Above this level, binding dramatically increases with smaller increases in receptor number. MM-302 does not effectively bind to or enter human cardiomyocytes. The level of MM-302 uptake into human cardiomyocytes is on the same order as untargeted pegylated liposomal doxorubicin. In contrast, the uptake of free doxorubicin is relatively much higher compared to both MM-302 and untargeted pegylated liposomal doxorubicin. The primary mechanism of action of MM-302 is the use of the HER2 protein to selectively deliver doxorubicin into tumor cells that express greater than approximately 200,000 HER2 receptors per cell.

Pharmaceutical Compositions

Pharmaceutical compositions suitable for administration to a patient are preferably in liquid form for intravenous administration.

In general, compositions typically comprise a pharmaceutically acceptable carrier. As used herein, the term "pharmaceutically acceptable" means approved by a government regulatory agency listed in the U.S. Pharmacopeia or another generally recognized pharmacopeia for use in animals, particularly in humans. The term "carrier" refers to a diluent, adjuvant, excipient, or vehicle with which the therapeutic agent is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline and aqueous dextrose and glycerol solutions may be employed as carriers, particularly for injectable solutions). Liquid compositions for parenteral administration can be formulated for administration by injection or continuous infusion. Routes of administration by injection or infusion include intravenous, intraperitoneal, intramuscular, intrathecal and subcutaneous. In one embodiment, both MM-302 and an anti-HER2 antibody are administered intravenously (e.g., separately or together over the course of a predetermined period of time, e.g., one hour).

MM-302 for intravenous infusion (e.g., over the course of one hour) is supplied as a clear liquid solution in sterile, single-use vials containing 10.1 ml of MM-302 at a concentration of 25 mg/ml in 20 mM histidine, 150 mM sodium chloride, pH 6.5, which should be stored at 2-8° C.

Doxorubicin is supplied in the hydrochloride form as a sterile red-orange lyophilized powder containing lactose and as a sterile parenteral, isotonic solution with sodium chloride and is also supplied as a sterile red-orange aqueous solution containing sodium chloride 0.9%. Doxorubicin is for IV use only.

Doxorubicin has the following structural formula:

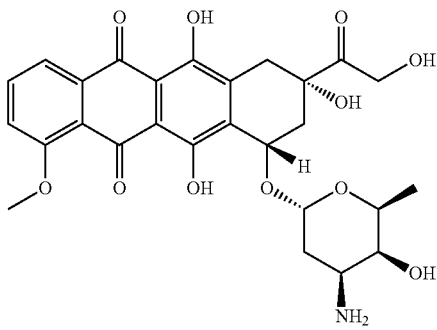 [SMILES: COc1cccc2c1C(=O)c1c(O)c3c(c(O)c1C2=O)C[C@@](O)(C(=O)CO)C[C@@H]3O[C@H]1C[C@H](N)[C@H](O)[C@H](C)O1]

Combination Therapy

According to the techniques herein, anti-HER2 antibodies may be administered in combination with MM-302 in order to effect improvement in subjects having breast cancer. In one embodiment, the anti-HER2 antibody is trastuzumab.

As used herein, adjunctive or combined administration (co-administration) may include simultaneous administration of the therapeutic agents in the same or different dosage form, or separate administration of the therapeutic agents (e.g., sequential administration of MM-302 and trastuzumab). For example, the additional therapeutic antibody (e.g., trastuzumab) may be simultaneously administered with MM-302, wherein both the additional therapeutic antibody and MM-302 are formulated together. Alternatively, the additional therapeutic antibody can be administered in combination with the MM-302, wherein both the additional therapeutic antibody and MM-302 are formulated for separate administration and are administered concurrently or sequentially. For example, MM-302 may be administered first, followed by the administration of the anti-HER2 therapeutic antibody. Alternatively, the therapeutic antibody may be administered first, followed by administration of MM-302. Such concurrent or sequential co-administration preferably results in both MM-302 and trastuzumab being simultaneously present in treated patients.

In another embodiment, an anti-HER2 antibody may be formulated for intravenous administration. In particular embodiments, the therapeutic antibody may be administered at a dose that ranges from about 100 mg/kg to about 1 mg/kg. In other embodiments, the therapeutic anti-HER2 antibody may be administered at a dose that ranges from about 50 mg/kg to about 2 mg/kg. In other embodiments, the therapeutic anti-HER2 antibody may be administered at a dose that ranges from about 40 mg/kg to about 3.22 mg/kg. In still other embodiments, the therapeutic anti-HER2 antibody may be administered as a dose of 40 mg/kg, 35 mg/kg, 30 mg/kg, 25 mg/kg, 20 mg/kg, 15 mg/kg, 12 mg/kg, 10 mg/kg, 8 mg/kg, 6 mg/kg, 4 mg/kg, and/or 3.2 mg/kg. In one embodiment, the dose of therapeutic antibody may be varied over time. For example, the therapeutic antibody may be initially administered at a high dose and may be lowered over time. In another embodiment, the therapeutic antibody is initially administered at a low dose and increased over time. In another embodiment, a dose of 40 mg/kg of anti-HER2 antibody may be administered once per week for two weeks, followed by a dose of 20 mg/kg of a therapeutic anti-HER2 antibody in combination with MM-302.

Treatment Protocols

Suitable treatment protocols include, for example, those wherein (A) the anthracycline-loaded immunoliposome (e.g., MM-302) may be administered to a patient (i.e., a human subject) once per every three weeks over a course of, e.g., fourteen three-week cycles (at a dose of 30-50 mg/m² per cycle), and (B) the anti-cancer therapeutic comprising a second anti-HER2 antibody is administered to a patient at least once per every three weeks over a course of fourteen three-week cycles.

In one embodiment, the anti-cancer therapeutic comprising a second anti-HER2 antibody (e.g., trastuzumab) may be administered in combination with an amount of MM-302 at an interval measured of at least seven days. A suitable weekly dosage of trastuzumab is 2 mg/kg.

In one embodiment, the first dose of the anthracycline-loaded immunoliposome and/or the second anti-HER2 antibody is a loading dose, i.e., a dose that is larger than the dose given in subsequent administrations (as such, the maintenance dose).

In another embodiment, MM-302 is administered once every three weeks or once every four weeks. The administration cycle may be repeated, as necessary.

In another embodiment, the amount of anti-cancer therapeutic comprising a second anti-HER2 antibody administered may be constant for each dose. In another embodiment, the amount of antibody administered may vary with each dose. For example, the maintenance (or follow-on) dose of the antibody may be higher than, or the same as, the loading dose that is first administered. In another embodiment, the maintenance dose of the antibody can be lower or the same as the loading dose.

In one embodiment, an anti-HER2 antibody may be administered as a monotherapy prior to at least one cycle of anti-HER2 antibody/MM-302 combination therapy. In one embodiment, anti-HER2 antibody monotherapy may be administered for two weeks, wherein the anti-HER2 antibody may be administered at 6 mg/kg the first week and at 4 mg/kg the second week.

In one embodiment, MM-302 may be administered as a monotherapy prior to at least one cycle of anti-HER2 antibody/MM-302 combination therapy. In one embodiment, the MM-302 monotherapy may be administered every four weeks, wherein the MM-302 may be administered at 30 mg/m², 40 mg/m², or 50 mg/m² once every four weeks.

Kits and Unit Dosage Forms

Also provided are kits that include a pharmaceutical composition containing an anthracycline-loaded anti-HER2 immunoliposome (e.g., MM-302), and a pharmaceutically-acceptable carrier, in a therapeutically effective amount adapted for use in the preceding methods. The kit may also include a pharmaceutical composition containing an anti-HER2 antibody (e.g., trastuzumab), and a pharmaceutically-acceptable carrier, in a therapeutically effective amount adapted for use in the preceding methods. The kits may optionally also include instructions, e.g., comprising administration schedules, to allow a practitioner (e.g., a physician, nurse, or patient) to administer the compositions contained therein to a patient having breast cancer, either alone or in combination. In one embodiment, the kit further comprises trastuzumab. In another embodiment the kit includes a syringe.

Optionally, the kits may include multiple packages of the single-dose pharmaceutical composition(s) containing an effective amount of the anti-HER2 antibody (e.g., trastuzumab) and/or an effective amount of an anthracycline-loaded anti-HER2 immunoliposome (e.g., MM-302) for a single administration or a combination administration in accordance with the methods provided above. Optionally, instruments or devices necessary for administering the pharmaceutical composition(s) may be included in the kits. For instance, a kit may provide one or more pre-filled syringes containing an amount of MM-302 that is about 100 times the dose in mg/kg indicated for administration in the above methods. Optionally, the kit may further comprise trastuzumab in a desired unit dosage form (e.g., a unit dosage form distributed by the manufacturer of trastuzumab) for administration. In another embodiment, a kit may further comprise doxorubicin.

The following Examples are merely illustrative and should not be construed as limiting the scope of this disclosure in any way as many variations and equivalents will become apparent to those skilled in the art upon reading the present disclosure.

EXAMPLES

Materials and Methods Used in these Examples

Materials: Doxorubicin is from SIGMA-ALDRICH, Inc. (St. Louis, Mo.). FITC-conjugated lectin (*lycopersicon esculentum* (tomato) lectin, Cat #FL-1171) is purchased from Vector Laboratories, Inc. (Burlingame, Calif.). Acetic acid, Methanol, and Acetonitrile are from EMD Chemicals Inc. (Gibbstown, N.J.). Water and Trifluoroacetic Acid (TFA) are from J. T. Baker (Phillipsburg, N.J.). HOECHST 33342 trihydrochloride trihydrate, ProLong Gold®, and DiIC18(5)-DS (DiI5) are from Invitrogen (Carlsbad, Calif.). Cholesterol and 1,2-distearoyl-sn-glycero-3-phosphoethanolamine-N-[amino(polyethylene glycol)-2000](ammonium salt) (PEG-DSPE) are from Avanti Polar Lipids Inc. Hydrogenated soy phosphatidylcholine (HSPC) is from Lipoid (Newark, N.J.). RPMI is from Lonza (Walkersville, Md.), Fetal Bovine Serum (FBS) is from Tissue Culture Biologicals and penicillin G/streptomycin sulphate mixture is from GIBCO (Invitrogen).

Preparation of immunoliposomes: Liposomes are prepared and loaded with doxorubicin using an ammonium sulfate gradient as previously described (Kirpotin et. al., Cancer Res. 2006; 66:6732-40; Park et al., Clin Cancer Res. 2002; 8:1172-81). The lipid components are HSPC, cholesterol, and PEG-DSPE (3:2:0.3, mol:mol:mol). The anti-ErbB2 (F5)-PEG-DSPE conjugate is prepared and inserted into the liposome to form immunoliposomes as reported by Nellis et al., (Biotechnol Prog. 2005; 21:205-20; Biotechnol Prog. 2005; 21:221-32). The DiI-5-labelled liposomes, MM-302-DiI5 and PLD-DiI5, are prepared as above with the difference that the DiIC18(5)-DS (DiI5) dye is solubilized with the lipid components at a concentration of 0.3 mol % of total phospholipid. In all cases unloaded free doxorubicin is removed using a Sephadex® G-75 size exclusion column eluted with Hepes buffered saline (pH 6.5). F5-lipo-DiI5 is prepared in a similar fashion as above but without doxorubicin, and incorporating an aqueous solution of HEPES buffered saline (pH 6.5).

Example 1

MM-302 and Trastuzumab Target Distinct Epitopes on HER2

MM-302 and trastuzumab are both HER2-targeted agents. Therefore, a co-localization experiment was performed. BT-474-M3 (see Noble, Cancer Chemother. Pharmacol. 2009 64:741-51) cells were co-incubated with DIi5-labeled MM-302 and 488-fluorophore-labeled trastuzumab (AlexaFluor® 488, Catalog Number A10235, Life Technologies). The results are shown in FIG. 1A. MM-302 (red, left panel) and trastuzumab (green, middle panel) both bind to the cell membrane, as further illustrated in the right panel, which shows overlapping binding of both MM-302 and trastuzumab (yellow).

Figure 1B:
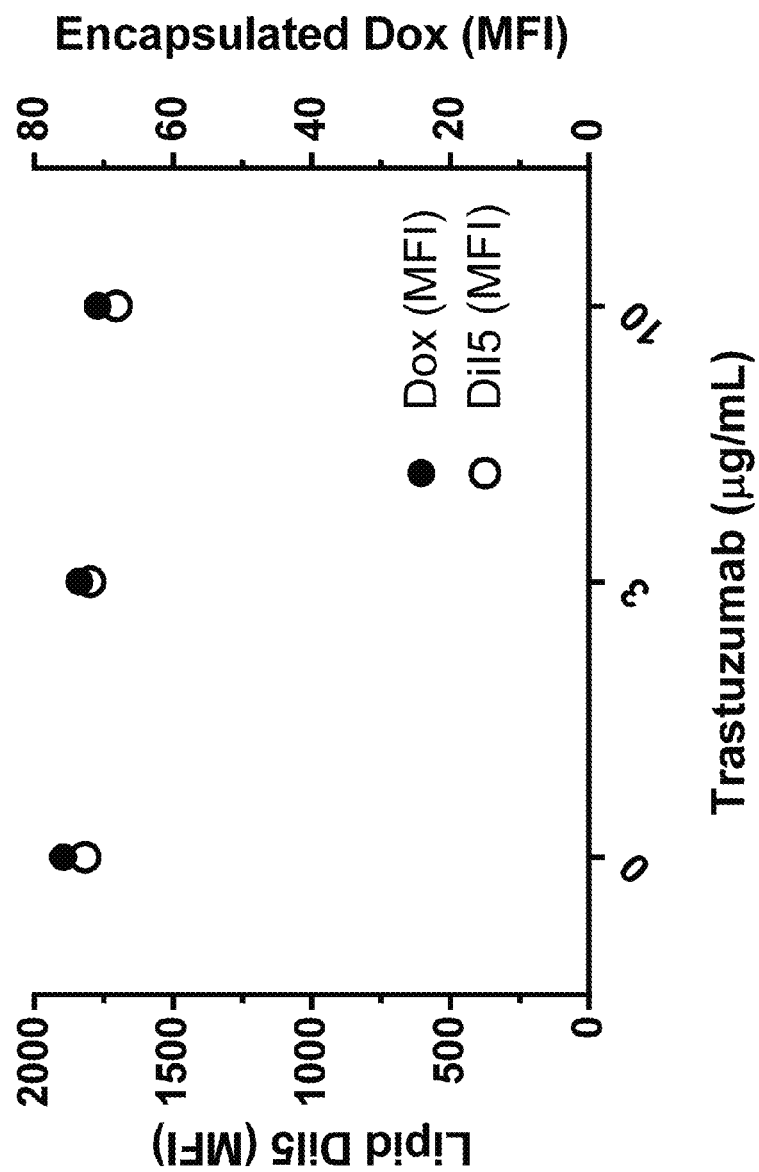
FIG. 1B is a graph showing that incubation of cells with trastuzumab does not prevent subsequent binding of MM-302. MCF7 cells expressing HER2 were first incubated with 0, 3, or 10 μg/ml trastuzumab (x-axis) and then exposed to 3 μg/ml fluorescently labeled (DIi5) MM-302. Cells were evaluated by flow cytometry for both DIi5 labeled lipid in the liposome (left y-axis as mean fluorescence intensity (MFI)) and doxorubicin encapsulated by the liposome (right y-axis as MFI).

In order to demonstrate that trastuzumab does not block MM-302 binding to HER2, MCF7 cells expressing HER2 were first incubated with 0, 3, or 10 μg/ml trastuzumab and then exposed to 3 μg/ml fluorescently labeled (DIi5) MM-302 for 3 hours at 37° C. After incubation, cells were washed and then evaluated by flow cytometry for both liposome signal (DIi5) and doxorubicin signal (Dox). As shown in FIG. 1B, incubation with trastuzumab did not prevent subsequent binding of MM-302 to the cells.

Example 2

The Combination of MM-302 and Trastuzumab in HER2-positive Cell Lines

Figure 2A:
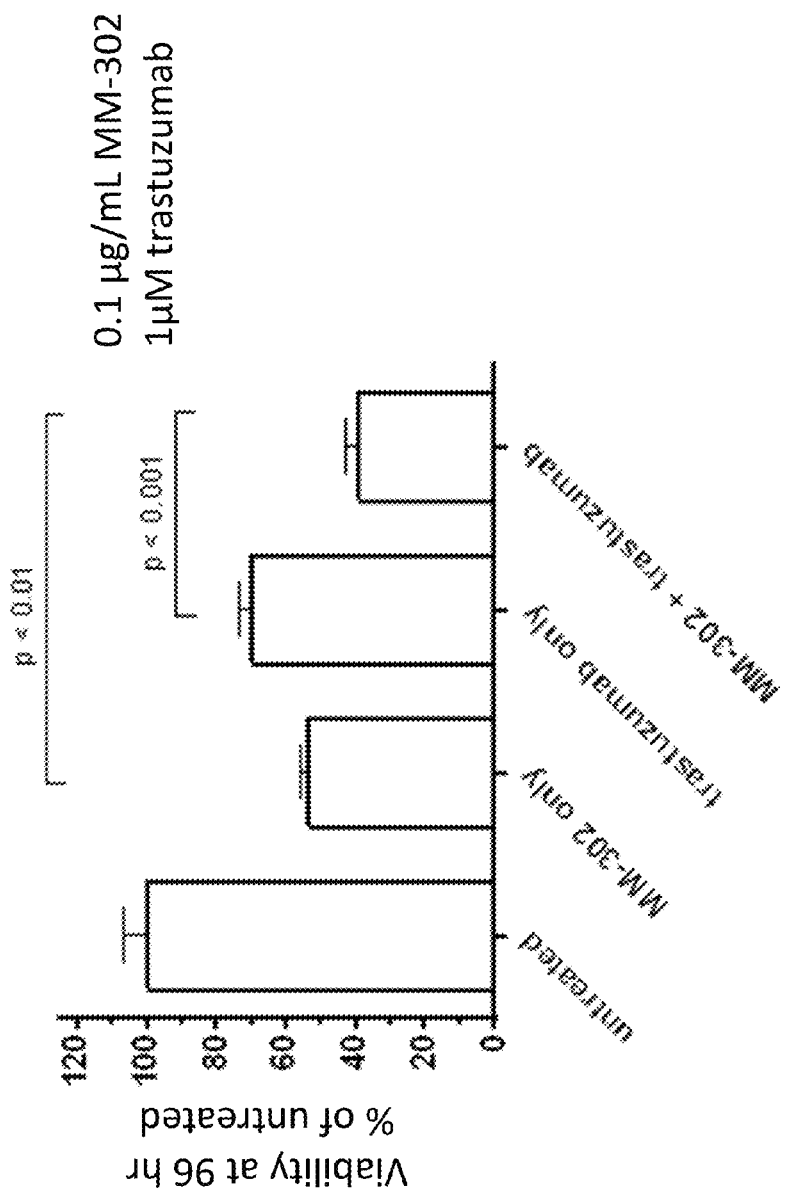
FIG. 2A is a graph showing that the combination of MM-302 and trastuzumab shows enhanced activity over single agents in the NCI-N87 HER2-positive cell line in vitro. NCI-N87 cells were tested with untreated, single agents (trastuzumab or MM-302) or the combination (MM-302+trastuzumab). Trastuzumab and MM-302 were used at 1 μM and 0.1 μg/mL, respectively, and agents were added simultaneously in the case of combination treatments. Cell viability was assessed at 96 hours using the PrestoBlue® cell viability reagent (Life Technologies) (shown on the y-axis as % of untreated control).

The MM-302+trastuzumab combination was tested against a broad panel of HER2-expressing cells lines. Twenty-nine HER2-expressing cell lines were treated with 1 μg/mL of MM-302, 1 μM trastuzumab, or the combination of MM-302 and trastuzumab (added simultaneously). Cell viability was assessed using the PrestoBlue® cell viability reagent (Life Technologies) at 96 hours relative to an untreated control. FIG. 2A shows viability data from NCI-N87 cells that were untreated or treated with MM-302 alone, trastuzumab alone or MM-302 plus trastuzumab. Increased cell killing is observed when cells are treated with MM-302 plus trastuzumab relative to either drug alone.

Figure 2B:
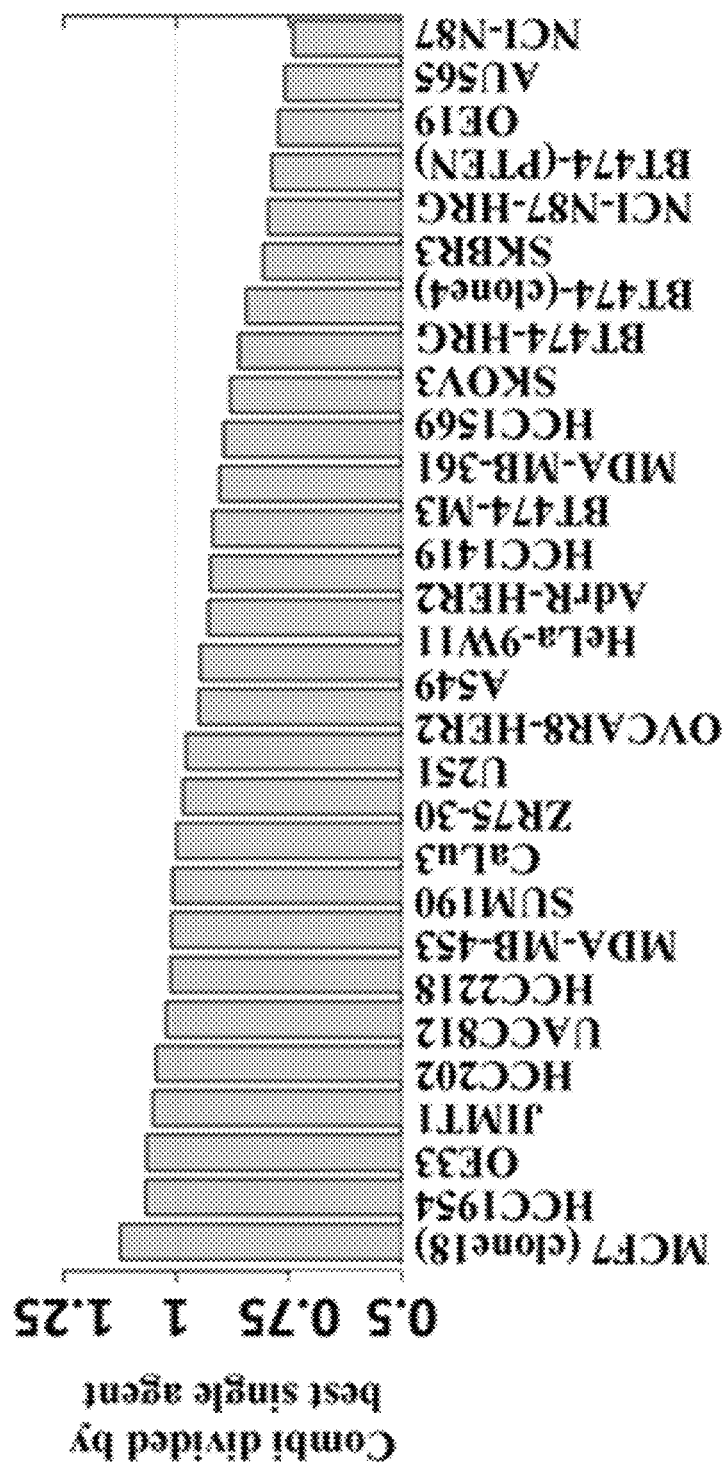
FIG. 2B is a graph showing that the combination of MM-302 and trastuzumab shows enhanced activity over single agents in a broad panel of HER2-positive cell lines in vitro. A panel of cell lines was treated as described for NCI-N87 cells in FIG. 2A. The effect of the combination relative to the best single agent is shown. Values less than 1 indicate a benefit of combining MM-302 and trastuzumab relative to either single agent.

Combinatorial benefit for each cell line was determined by dividing the viability of cells treated with the combination of MM-302 plus trastuzumab vs. the best response to either MM-302 or trastuzumab alone. As summarized in Example 2 below, in nearly all cases the combination of MM-302 and trastuzumab reduced cell viability relative to the most effective single agent. Furthermore, in approximately 62% (18/29) of the cell lines the combination was more effective than either single agent alone. Results are shown in FIG. 2B. A summary of the cell lines used is in the table below.

| CELL LINE | CAT #/Tissue Source Type | Modification |
|---|---|---|
| A549 | Lung ATCC ® #CCL-185 ™ | |
| AdrR-HER2 (NCI/ADR-RES) | Breast, multidrug resistant NCI-60 panel of cell lines | Engineered to stably express HER2 |
| AU565 | Breast ATCC ® CRL-2351 ™ | |
| BT474-clone 4 | Breast ATCC ® HTB-20 ™ | |
| BT474-(PTEN) | Breast ATCC ® HTB-20 ™ | Engineered to stably express PTEN |
| BT474-HRG | Breast ATCC ® HTB-20 ™ | Engineered to stably express Heregulin1-β1 |
| BT474-M3 | Breast ATCC ® HTB-20 ™ | See Noble, Cancer Chemother. Pharmacol. 2009 64: 741-51 |
| CaLu3 | Lung ATCC ® HTB-55 ™ | |
| HCC1419 | Breast ATCC ® CRL-2326 ™ | |
| HCC1569 | Breast ATCC ® CRL-2330 ™ | |
| HCC1954 | Breast (ATCC ® CRL-2338 ™) | |
| HCC202 | Breast ATCC ® CRL-2316 ™ | |
| HCC2218 | Breast ATCC ® CRL-2343 ™ | |
| HeLa-9W11 | cervical ATCC ® CCL-2 ™ (HeLa) | Engineered to stably express HER2 using neomycin-selectable expression vector Z2866, GeneCopeia |
| JIMT-1 | Breast carcinoma DSMZ No.: ACC 589 | |
| MCF7 (CLONE 18) | Breast ATCC ® HTB-22 ™ | |
| MDA-MB-361 | Breast ATCC ® HTB-27 ™ | |
| MDA-MB-453 | Breast ATCC ® HTB-131 ™ | |
| NCI-N87 | Gastric ATCC ® # CRL-5822 ™ | |
| NCI-N87-HRG | Gastric ATCC ® # CRL-5822 ™ | Engineered to stably express Heregulin1-β1 |
| OE19 | Esophageal adenocarcinoma DSMZ No.: ACC 700 | |
| OE33 | esophageal carcinoma | |
| OVCAR8-HER2 | ovarian adenocarcinoma ATCC ® #HTB-161 ™ | Engineered to stably express HER2 |
| SKBR3 | Breast ATCC ® HTB-30 ™ | |
| SKOV3 | Ovarian ATCC ® HTB-77 ™ | |

-continued

| CELL LINE | CAT #/Tissue Source Type | Modification |
|---|---|---|
| SUM190 | Breast Asterand ® | |
| U-251 | Brain 09063001-1VL, Sigma | |
| UACC812 | Breast ATCC ® CRL-1897 ™ | |
| ZR75-30 | Breast ATCC ® CRL-1504 ™ | |

Example 2

MM-302 In Vivo Pharmacology

Figure 3A:
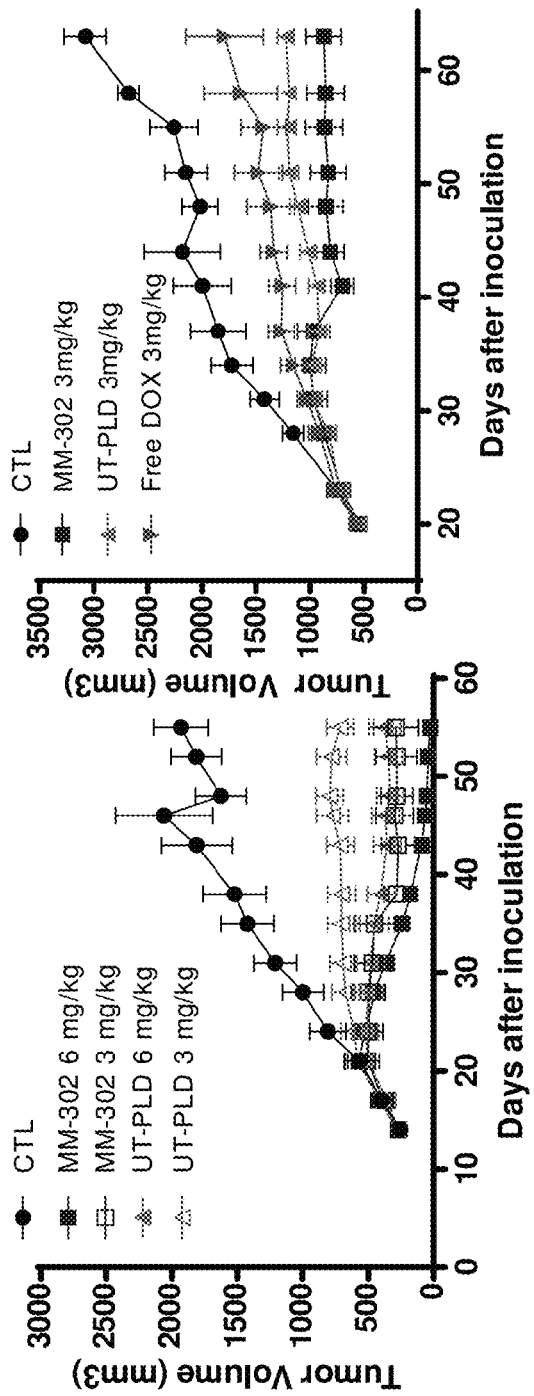
In FIG. 3A (BT-474-M3) and 3B (NCI-N87), two studies were performed for each tumor model (left and right hand panels), and tumor size was measured twice per week in each study. In the left hand panels of 3A and 3B, the activity of MM-302 at 3 mg/kg or 6 mg/kg is compared to that of untargeted liposome (UT-PLD) at the same concentrations. In the right hand panels of 3A and 3B, the activity of MM-302 is compared to that of UT-PLD and free doxorubicin, all dosed at 3 mg/kg. MM-302 was more potent than free doxorubicin as well as UT-PLD in inhibiting tumor growth.
Figure 3B:
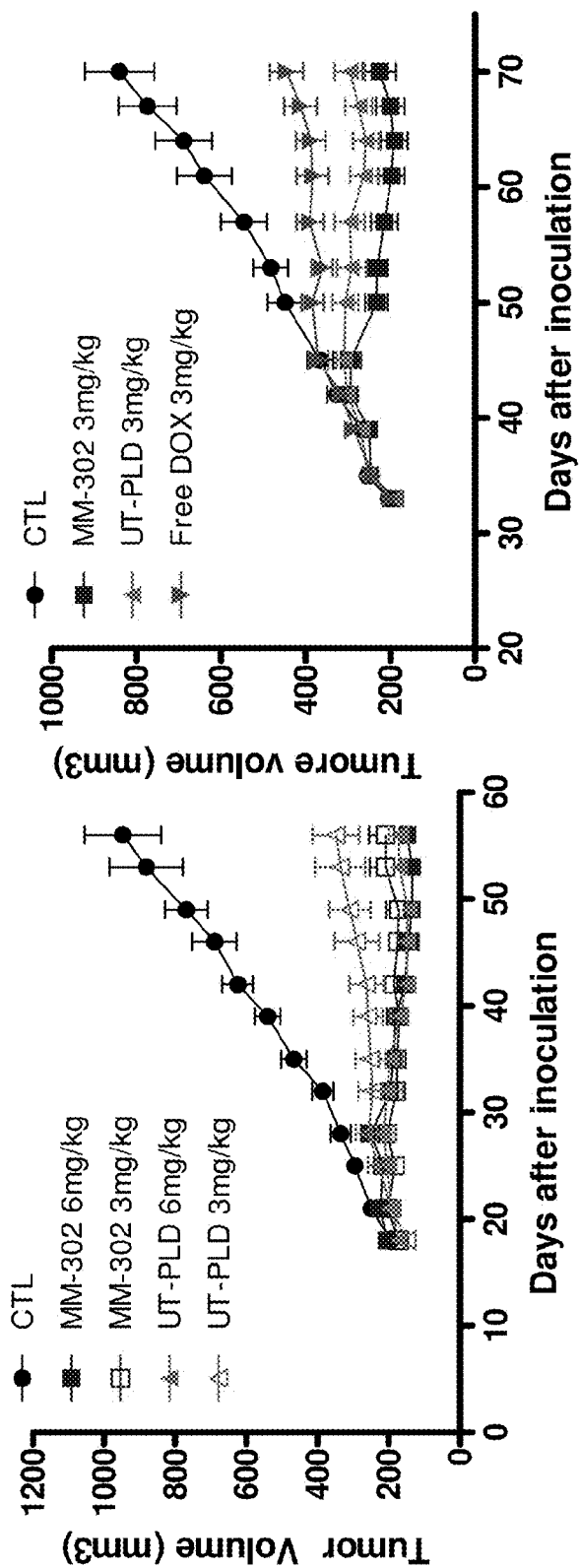
FIG. 3 shows six graphs demonstrating the anti-tumor activity of MM-302 in breast (BT-474-M3) and gastric (NCI-N87) xenograft models.
As shown in FIG. 3C, MM-302 and trastuzumab administered in combination with one another were more active than either agent alone when tested in the same HER2-overexpressing breast (left panel) and gastric (right panel) models shown in FIGS. 3A and 3B.

MM-302 was tested in two tumor xenograft models using a human breast cancer line (BT-474-M3) and a human gastric cancer line (NCI-N87), both of which overexpress HER2. MM-302 was dosed at 3 mg/kg weekly for 3 weeks and trastuzumab was dosed at 3.5 mg/kg every 3 days. Two studies were performed for each tumor model and tumor size was measured twice per week in each study. As shown in FIGS. 3A (BT-474-M3) and 3B (NCI-N87), MM-302 was significantly more potent than free doxorubicin in inhibiting tumor growth. Analysis of blood samples taken from mice demonstrated that MM-302 and the untargeted liposomal doxorubicin displayed similar pharmacokinetic profiles, suggesting that the differences in anti-tumor activity of MM-302 and untargeted liposomal doxorubicin were unlikely to be due to differences in pharmacokinetics, and likely attributable to HER2-targeting.

Figure 3C:
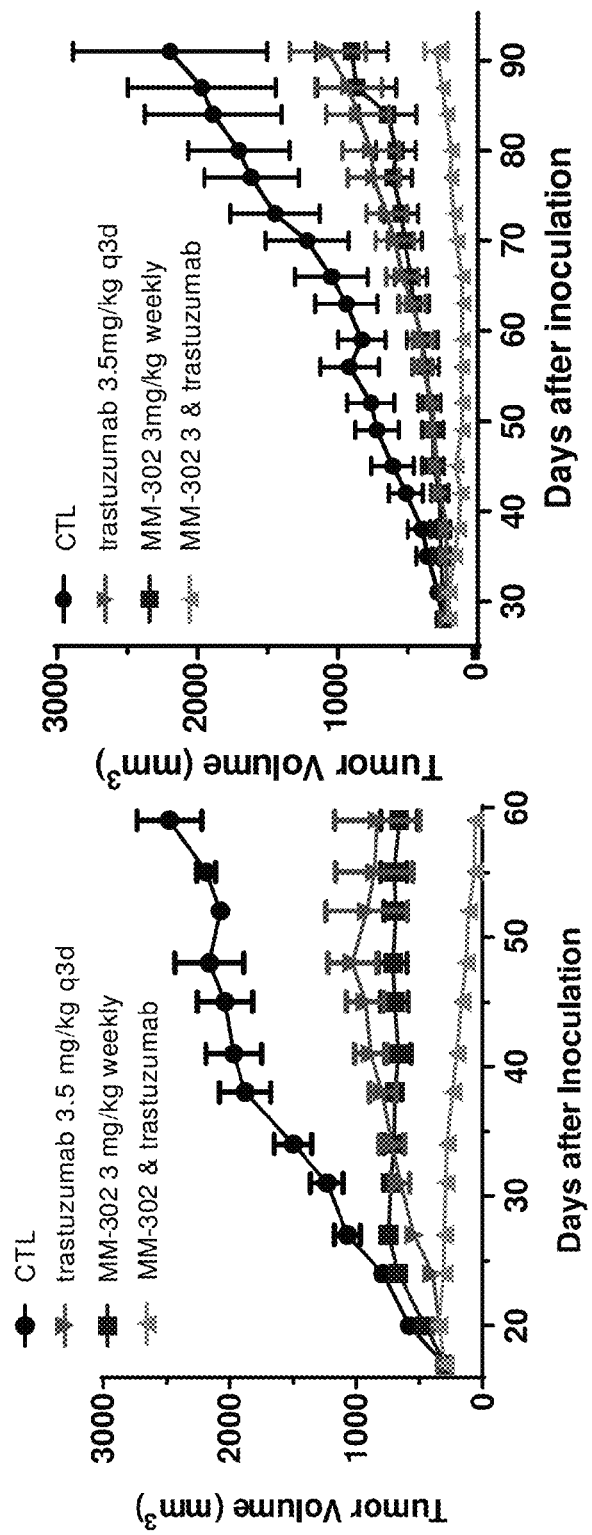
Figure 4A:
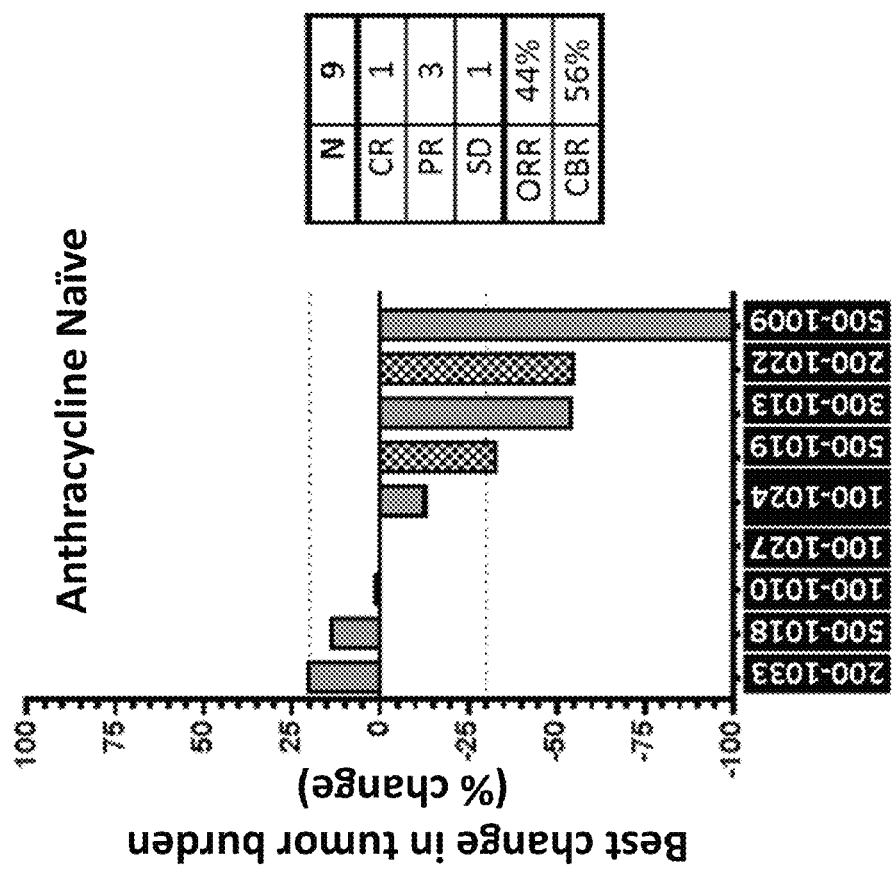
FIG. 4 illustrates 9 anthracycline naive (4A and 4C) and 15 anthracycline exposed (4B and 4D) patients who have been treated with 30, 40 or 50 mg/m$^2$ of MM-302 monotherapy. In the anthracycline naïve subgroup, 1 patient had a complete response (CR) and 3 patients had a partial response (PR) (4A) whereas no patients in the anthracycline exposed subgroup had a response (4B). Anthracycline naïve patients had a median progression free survival (PFS) of 10.9 months (95% confidence interval (CI): 1.6-NR) (4C) while anthracycline-exposed patients had a median PFS of 5.6 months (95% CI: 1.9-8.6) (4D). Solid bars represent patients that are off study and checkered bars represent patients that are still on study.
Figure 4B:
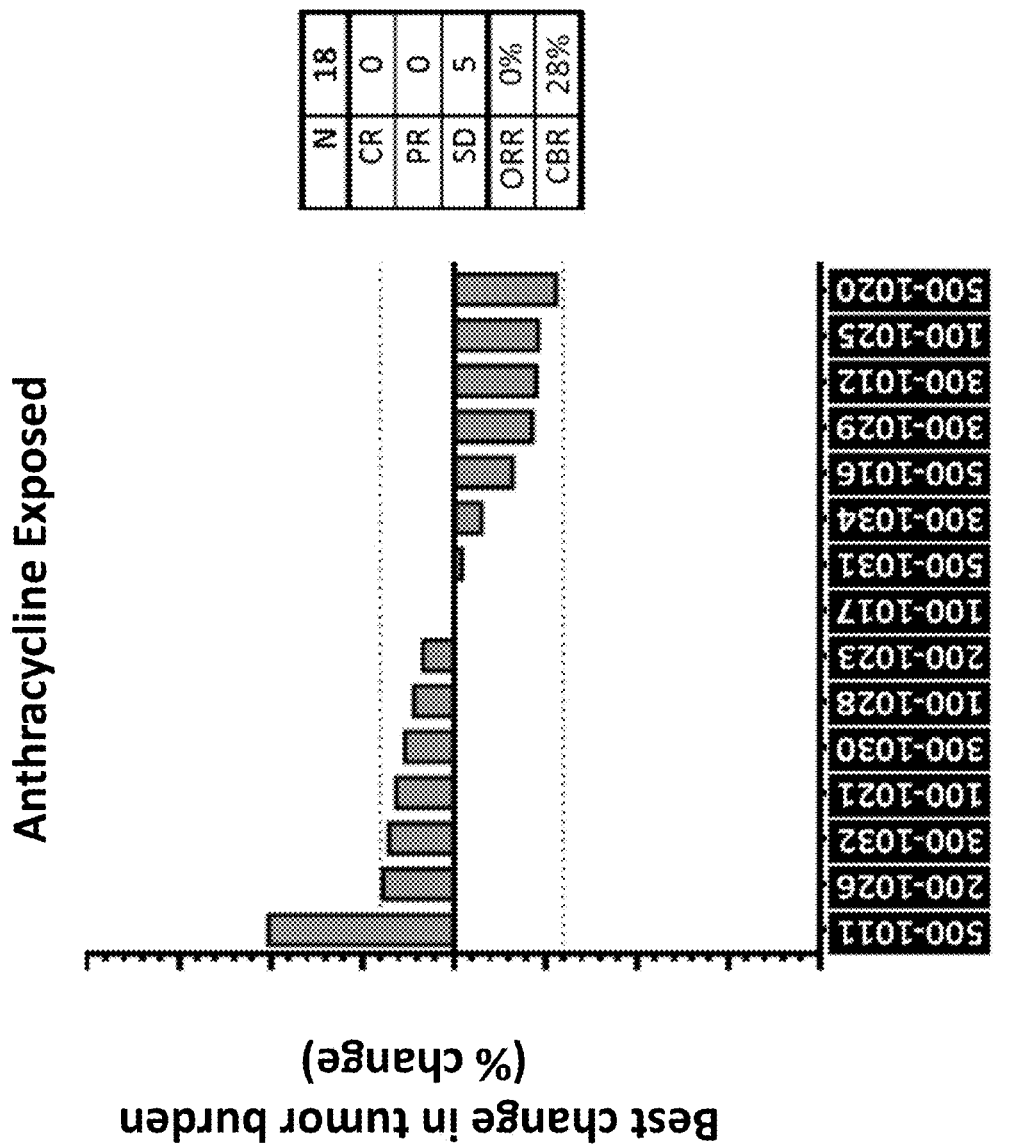
Figure 4C:
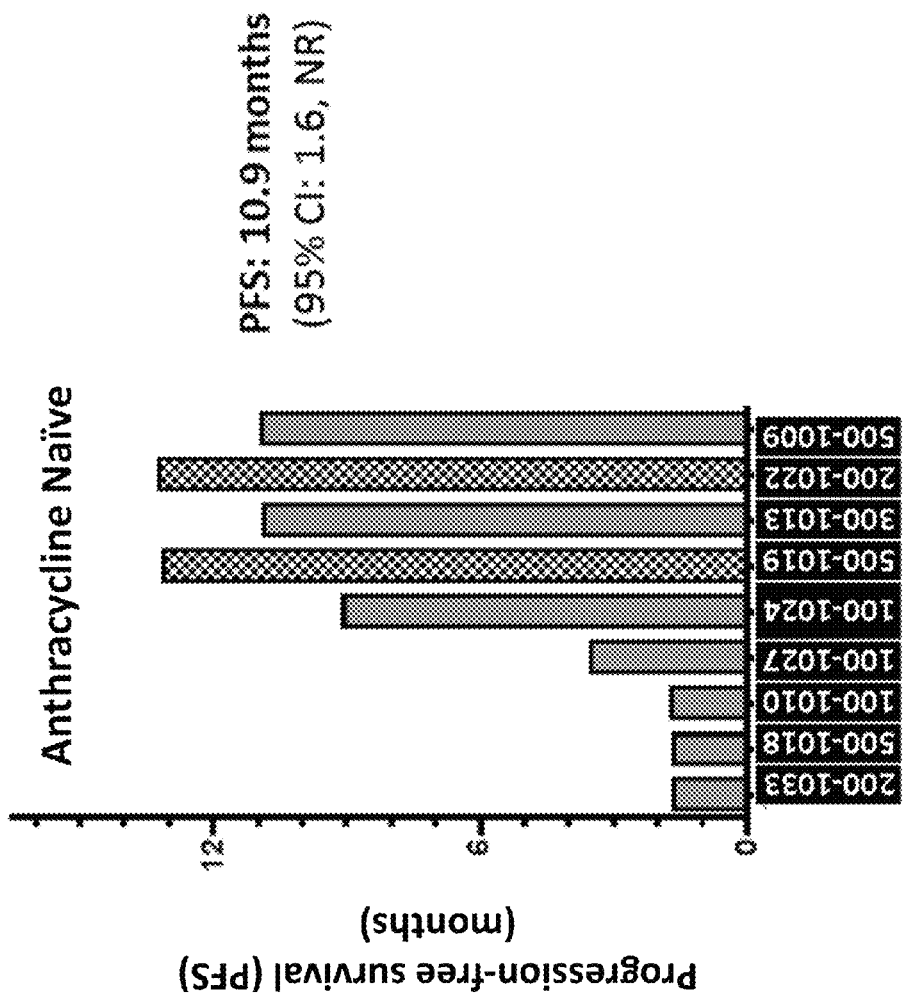
Figure 4D:
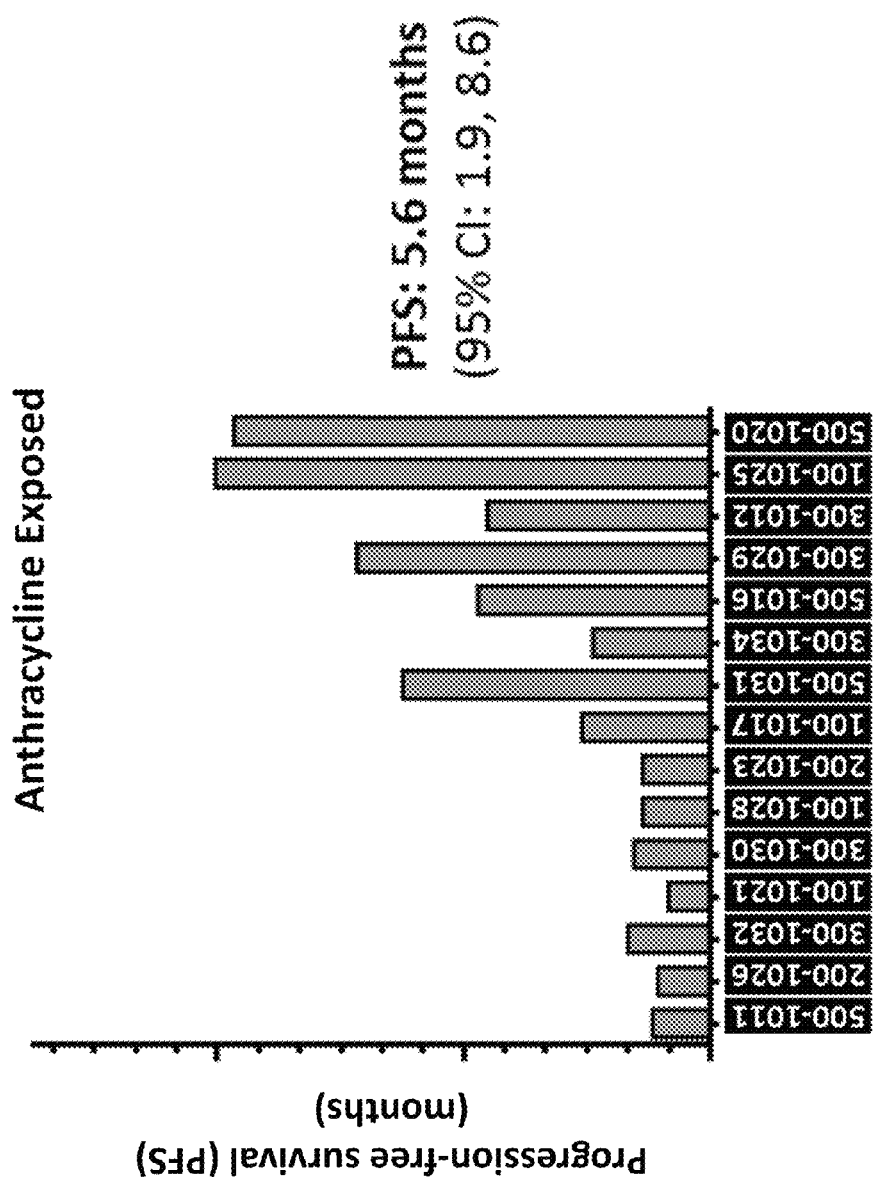
Figure 5A:
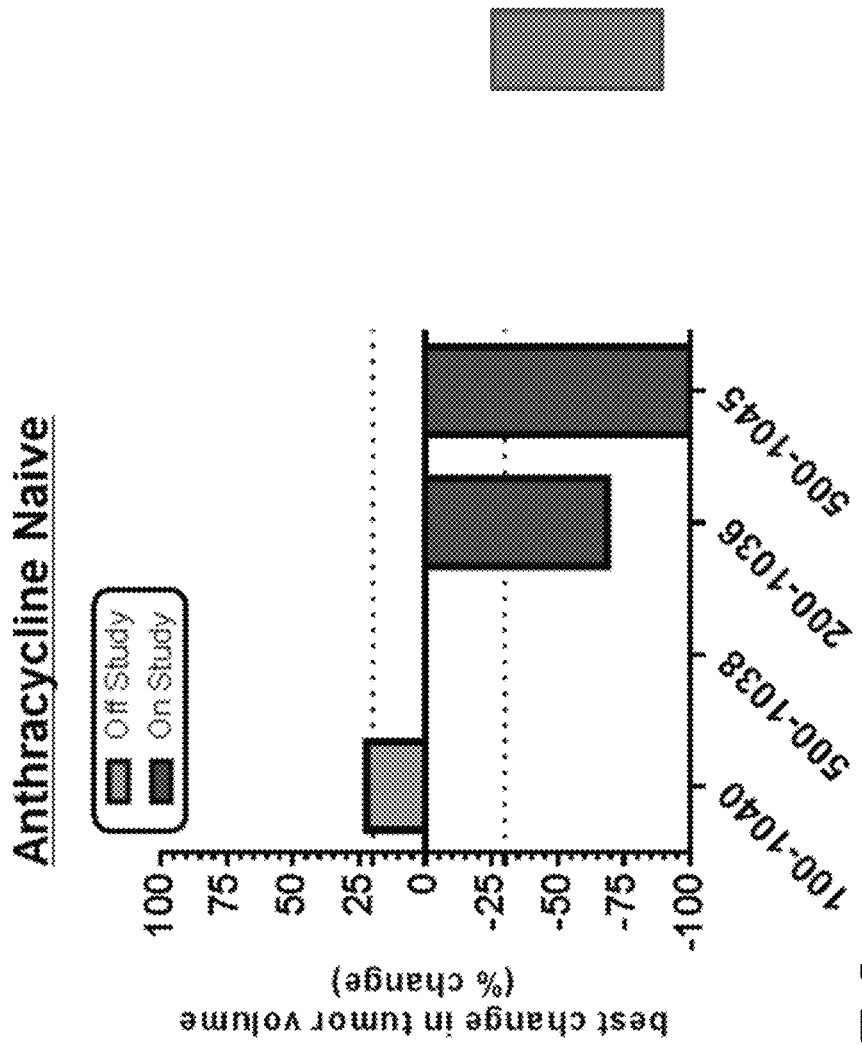
FIG. 5 is four graphs showing the change in tumor volume for anthracycline naïve (5A) and exposed (5B) patients receiving 30, 40 and 50 mg/m$^2$ of MM-302 monotherapy. PFS for anthracycline naïve (5C) and exposed (5D) patients. Patients 500-1038, 200-1036, 500-1042 and 500-1045 are continuing on study; the other patients are off study.
Figure 5B:
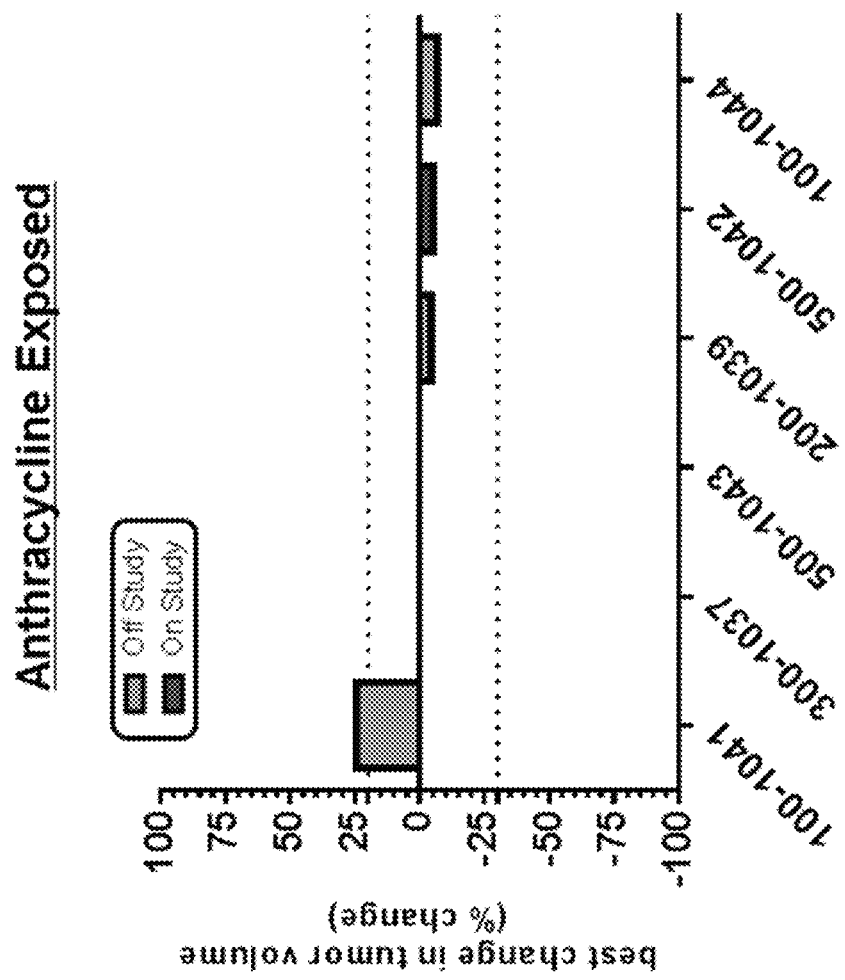
Figure 5C:
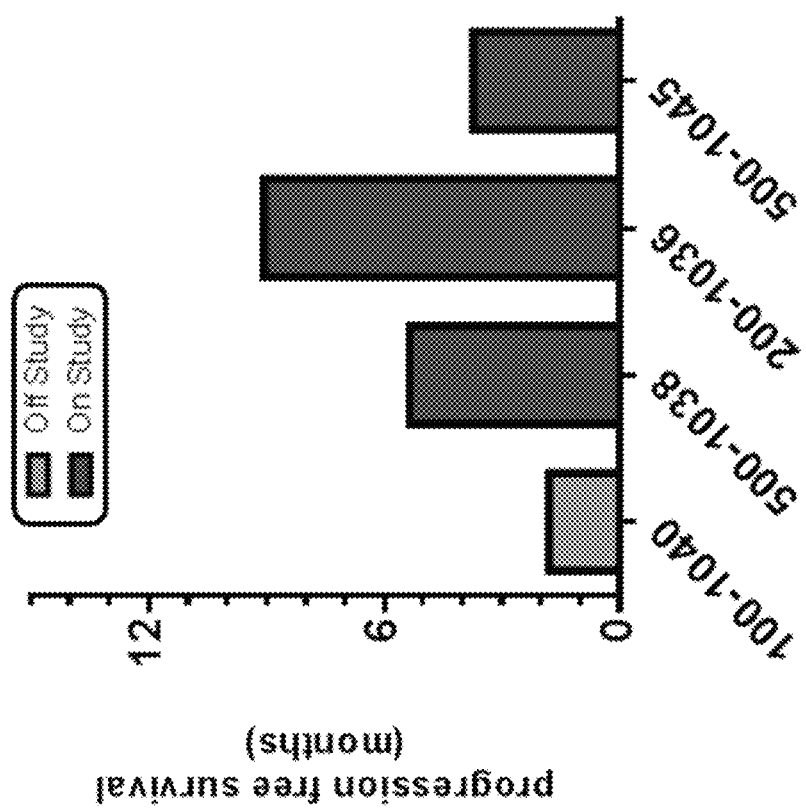
Figure 5D:
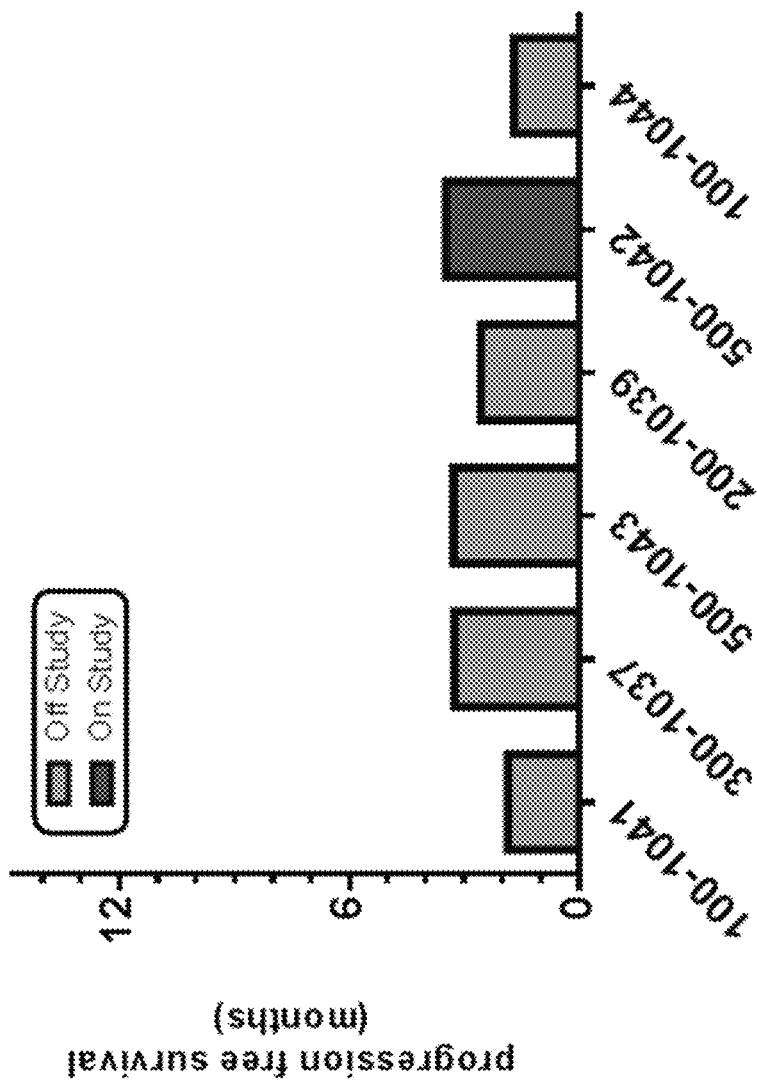

As shown in FIG. 3C, MM-302 and trastuzumab administered in combination with one another were more active than either agent alone when tested in the same breast and gastric models that overexpress HER2. By applying response criteria similar to that which is used to evaluate tumor response in the clinic, one can categorize the tumors as Responders, Stable Disease (SD) or Progressive Disease (PD) based on percent tumor change. In applying this evaluation to the data from FIG. 2, it was observed that when MM-302 and trastuzumab are combined, there were greatly improved response rates in both the BT-474-M3 and NCI-N87 models (Table E1) demonstrating a greater than additive activity and therapeutic potential of combining these agents in HER2-expressing cancers.

TABLE E1

Administration of trastuzumab increases the response rate to MM-302*

| Tumor Model | Treatment Arm | PD | SD | Responders |
|---|---|---|---|---|
| BT-474-M3 | MM-302, 3 mg/kg | 8 (80%) | 1 (10%) | 1 (10%) |
| BT-474-M3 | trastuzumab | 5 (50%) | 4 (40%) | 1 (10%) |
| BT-474-M3 | MM-302, 3 mg/kg + trastuzumab | 2 (20%) | 2 (20%) | 6 (60%) |
| NCI-N87 | MM-302, 3 mg/kg | 0 | 9 (100%) | 0 |
| NCI-N87 | trastuzumab | 0 | 7 (78%) | 2 (22%) |
| NCI-N87 | MM-302, 3 mg/kg + trastuzumab | 0 | 2 (22%) | 7 (78%) |

*Anti-tumor responses were classified using the following criteria: Tumors that grew >20% in volume from baseline were categorized as 'Progressive Disease (PD)'. Tumors growing <20% and shrinking <30% were classified as 'Stable Disease (SD)'. Tumors shrinking >30% were classified as 'Responders'.

Example 3

Patient Selection Criteria for MM-302 and/or Trastuzumab Treatment

In this Example, patients eligible for monotherapy MM-302 treatment are positive for advanced breast cancer (e.g., locally advanced/unresectable or metastatic). Patients eligible for MM-302 monotherapy and also the MM-302 and trastuzumab combination cohorts are positive for advanced HER2 positive cancer. Patients should also have Eastern Cooperative Oncology Group (ECOG) Performance Score (PS) of 0 or 1.

Additionally, eligible patients have adequate bone marrow reserves as evidenced by: 1) absolute neutrophil count (ANC) ≥1,500/μL, 2) platelet count ≥100,000/μL, and 3) Hemoglobin ≥9 μg/dL (Transfusions allowed). Eligible patients also have adequate hepatic function as evidenced by: 1) serum total bilirubin within normal limits and 2) aspartate aminotransferase (AST), Alanine aminotransferase (ALT) up to 2× upper limit of normal. Additionally, eligible patients also have adequate renal function as evidenced by a serum creatinine ≤1.5×ULN. Patients have adequate cardiac function as evidenced by a measured left ventricular ejection fraction of ≥50% by ECHO or MUGA within approximately 28 days of study entry.

In some embodiments, patients have anthracycline naïve, advanced/metastatic HER2-positive breast cancer. In further embodiments, patients have been previously treated with trastuzumab and T-DM1.

Example 4

Activity of MM-302 monotherapy in Anthracycline-Naïve and Anthracycline-Exposed Patients 27 patients were treated with therapeutic doses of 30, 40 and 50 mg/m$^2$ MM-302 monotherapy, 18 patients had received prior treatment with an anthracycline and nine patients were anthracycline naïve (Table E2 and FIG. 4). Of the 18 patients previously treated with anthracyclines, 16 (89%) of those patients had previously been treated with an anthracycline-containing regimen for neoadjuvant or adjuvant disease, and none of these patients had previously been re-challenged with an anthracycline in the metastatic setting. The two patients previously treated with an anthracycline in the metastatic setting had received PLD and had not received prior anthracycline based therapy for the early treatment of their disease.

TABLE #E2

| | MM-302 monotherapy\ (30, 40, 50 mg/m$^2$) | | |
|---|---|---|---|
| | Anthracycline Naïve | Anthracycline Exposed | Total |
| Patients | N = 9 | N = 18 | N = 27 |
| Median PFS in Months (95% CI) | 10.9 (1.6, NR) | 5.6 (1.9, 8.6) | 5.6 (2.8, 10.9) |
| Evaluable, n | 9 | 18 | 27 |
| CR, n | 1 | 0 | 1 |
| PR, n | 3 | 0 | 3 |
| SD (≥24 weeks), n | 1 | 5 | 6 |
| PD, n | 3 | 4 | 7 |
| ORR | 44.4% | 0% | 14.8% |
| CBR | 55.6% | 27.8% | 37.0% |
| Prior Number of Therapies for Metastatic Disease | | | |
| Median | 2 | 5 | 4 |
| Minimum | 1 | 1 | 1 |
| Maximum | 10 | 9 | 10 |

Kaplan-Meier estimates of median progression-free survival (PFS) show that on average, the anthracycline naïve group had a median PFS of 10.9 months (95% CI; 1.6—Not Reached), which was higher than the 5.6 months (95% CI; 1.9-8.6) observed in the anthracycline-exposed group. Patients experiencing a CR and a PR treated with MM-302 monotherapy were anthracycline naïve prior to receiving MM-302. A similar improvement in benefit is observed with respect to ORR and CBR between the anthracycline exposed and naive groups. An ORR 44% vs. 0% and CBR of 56% vs. 28%, respectively, were seen in the anthracycline naïve vs. exposed patients.

As shown in FIG. 4, 9 anthracycline-naïve and fifteen anthracycline-exposed patients were treated with 30, 40 or 50 mg/m$^2$ of MM-302 monotherapy. In the anthracycline naïve subgroup, 1 patient had a complete response (CR) and 3 patients had a partial response (PR) (FIG. 4A) whereas no patients in the anthracycline exposed subgroup had a response (FIG. 4B). Anthracycline naïve patients had a median progression free survival (PFS) of 10.9 months (95% confidence interval (CI): 1.6-NR) (FIG. 4C) while anthracycline exposed patients had a median PFS of 5.6 months (95% CI: 1.9-8.6) (FIG. 4D).

Example 3

MM-302 (30 mg/m$^2$)/Trastuzumab (4 mg/kg) Combination Therapy

Patients diagnosed with a HER2-positive cancer are treated with the combination of MM-302 and trastuzumab as follows:

As shown in Table E2, MM-302 is administered at a dose of 30 mg/m$^2$ once every 4 weeks by intravenous injection over a 60 minute period of time. Trastuzumab is administered at a dose of 4 mg/kg every two weeks (the first dose of trastuzumab is a loading dose of 6 mg/kg administered over 90 minutes followed by dosing every two weeks at 4 mg/kg over 30-90 minutes via IV infusion).

TABLE E2

| MM-302 Dose (mg/m$^2$) Q4W | Trastuzumab Maintenance Dose (mg/kg) Q2W |
|---|---|
| 40 | 4 |

Example 4

MM-302 (40 mg/m$^2$)/Trastuzumab (4 mg/kg) Combination Therapy

Patients diagnosed with a HER2-positive cancer are treated with the combination of MM-302 and trastuzumab as follows:

As shown in Table E3, MM-302 is administered at a dose of 40 mg/m$^2$ once every 4 weeks by intravenous injection over a 60 minute period of time. The first dose of MM-302 is administered as a monotherapy. Trastuzumab is then administered at a dose of 4 mg/kg every two weeks (the first dose of trastuzumab is a loading dose of 6 mg/kg administered over 90 minutes followed by dosing every two weeks at 4 mg/kg over 30-90 minutes via IV infusion).

TABLE E3

| MM-302 Dose (mg/m$^2$) Q4W | Trastuzumab Maintenance Dose (mg/kg) Q2W |
|---|---|
| 40 | 4 |

Example 6

MM-302 (30 mg/m$^2$)/Trastuzumab (6 mg/kg) Combination Therapy

Patients diagnosed with a HER2-positive cancer are treated with the combination of MM-302 and trastuzumab as follows:

As shown in Table E4, MM-302 is administered at a dose of 30 mg/m$^2$ once every 3 weeks by intravenous injection over a 60 minute period of time. Trastuzumab is then administered at a dose of 6 mg/kg every three weeks (the first dose of trastuzumab is a loading dose of 8 mg/kg administered over 90 minutes followed by every three weeks dosing at 6 mg/kg over 30-90 minutes via IV infusion).

TABLE E4

| MM-302 Dose (mg/m$^2$) Q3W | Trastuzumab Dose (mg/kg) Q3W |
|---|---|
| 30 | 6 |

Example 7

MM-302 (40 mg/m$^2$)/Trastuzumab (6 mg/kg) Combination Therapy

Patients diagnosed with a HER2-positive cancer are treated with the combination of MM-302 and trastuzumab as follows:

As shown in Table E5, MM-302 is administered at a dose of 40 mg/m$^2$ once every 4 weeks by intravenous injection over a 60 minute period of time. Trastuzumab is then administered at first loading dose of 8 mg/kg during the first cycle followed by a maintenance dose of 6 mg/kg every two weeks). Trastuzumab is administered over 90 minutes over 30-90 minutes via IV infusion).

TABLE E5

| MM-302 Dose (mg/m$^2$) Q3W | Trastuzumab Maintenance Dose (mg/kg) Q3W |
|---|---|
| 40 | 6 |

Example 8

MM-302 and Trastuzumab in Anthracycline Naïve and Anthracycline Exposed Patients In the patients treated with MM-302 plus trastuzumab, eight patients were anthracycline-exposed while five patients were anthracycline naïve. In this group, 2 of the 4 patients who were anthracycline naive experienced a PR and 3 of the 4 remain on study, receiving at least 5 cycles of treatment at the time of this analysis. One anthracycline naïve patient treated with the combination of MM-302 plus trastuzumab who came off study was previously treated with T-DM1. Immunohistochemistry analysis of a biopsy taken following the first dose of MM-302 plus trastuzumab indicate this patient's tumor was HER2 "0" by IHC at the start of MM-302 treatment. These results may explain the lack of activity in this patient and is consistent with an emerging hypothesis that one of the acquired resistance mechanisms for T-DM1 is down-regulation of HER2 signaling. Available data are summarized below in Table E6 and shown in FIG. 5. Estimates of PFS, ORR and CBR have been omitted due to the very small sample size as at the time of analysis.

TABLE E6

Comparison of MM-302 response rates with trastuzumab in anthracycline naive and anthracycline exposed patients

| | MM-302 (30, 40, 50 mg/m$^2$) + Trastuzumab (4/2 mg/kg) | | |
|---|---|---|---|
| Patients | N = 5 | N = 8 | N = 13 |
| Evaluable, n | 4 | 7 | 11 |
| CR, n | 0 | 0 | 0 |
| PR, n | 2 | 0 | 2 |
| SD (≥24 weeks), n | 1 | 0 | 1 |
| PD, n | 1* | 1 | 2 |
| Prior Number of Therapies for Metastatic Disease | | | |
| Median | 2 | 4.5 | 3 |
| Minimum | 0 | 0 | 0 |
| Maximum | 6 | 11 | 11 |

*patient biopsy was subsequently found to be HER2-negative (HER2 IHC 0 and FISH negative)

Example 9

Figure 6:
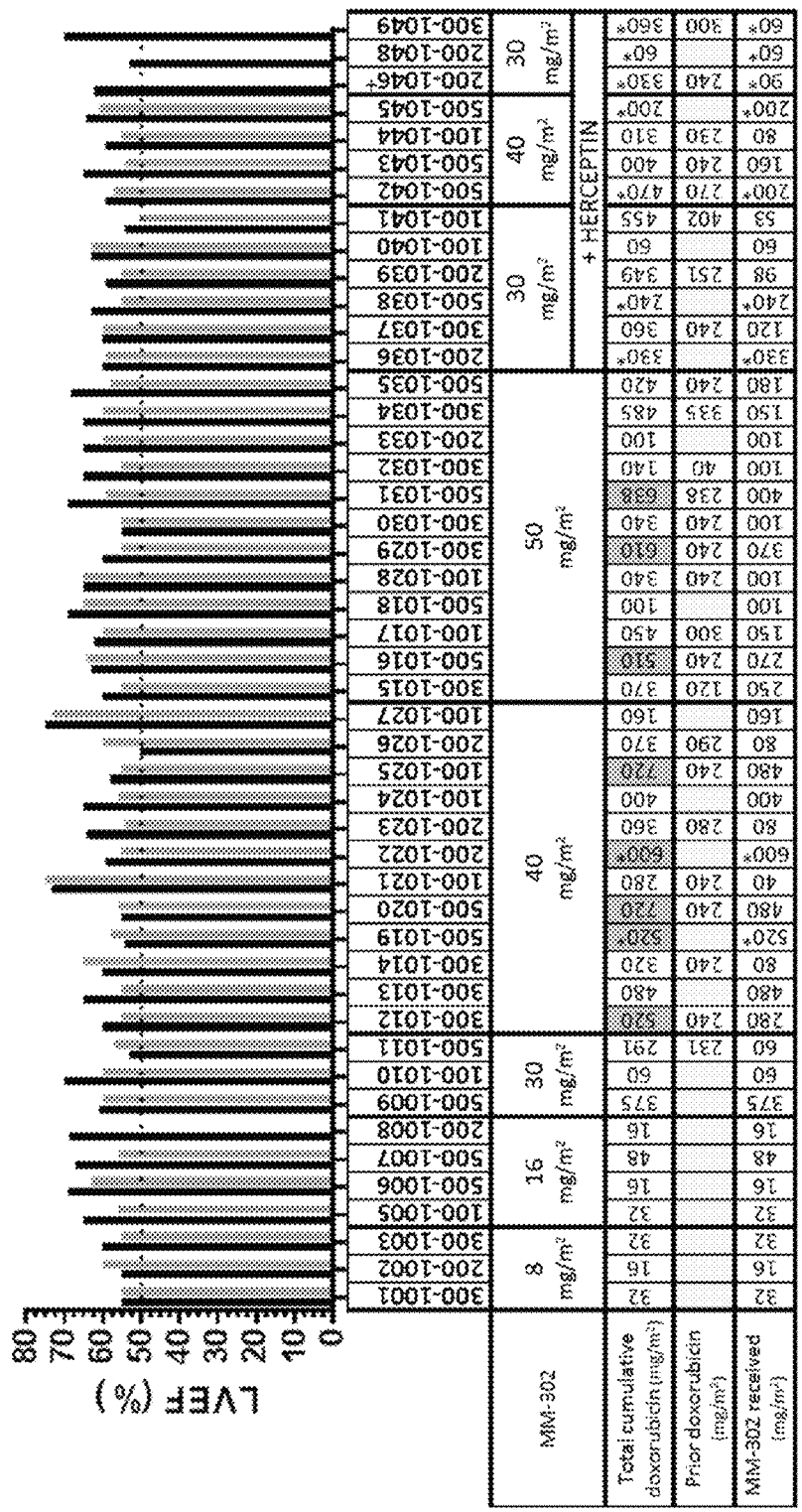
FIG. 6 is a graph and a table demonstrating the cardiac safety of MM-302 monotherapy and MM-302+trastuzumab therapy. No clinically significant left ventricular ejection fraction (LVEF) declines were observed for the 47 patients assessed in this analysis. LVEF measurements are shown in pairs of baseline (grey) and the lowest reading post-baseline (black). The horizontal black line identifies 50% LVEF. Total cumulative doxorubicin, prior doxorubicin exposure and amount of MM-302 received on study are shown. Values in shaded boxes identify patients receiving >500 mg/m² total cumulative doxorubicin. *identifies patients still on study. +following the data cut, one patient experienced a reduction in LVEF <50% and >10 absolute percentage points from baseline that was not congestive heart failure. Upon reassessment LVEF recovered to >50% and patient is continuing treatment.

Safe Use of Anthracyclines in Combination Therapy with Anti-HER2 Antibodies to Treat HER2-positive Metastatic Breast Cancer As shown in FIG. 6, in the ongoing clinical trial, patients receiving a range of doses of MM-302 monotherapy or MM-302+trastuzumab combination therapy had not experienced a decline in LVEF following treatment. This was observed even for patients who received greater than 500 mg/m$^2$ of cumulative doxorubicin (although a single patient in the study did subsequently exhibit a decline in LVEF). These data show that MM-302 may be administered safely to patients as monotherapy or in combination with other HER2-targeted therapeutics.

Equivalents

Those skilled in the art will recognize, or be able to ascertain and implement using no more than routine experimentation, many equivalents of the specific embodiments described herein. Such equivalents are intended to be encompassed by the following claims. Any combination, or combinations, of the embodiments disclosed in the dependent claims are contemplated to be within the scope of the disclosure.

INCORPORATION BY REFERENCE

The disclosure of each and every U.S. and foreign patent and pending patent application and publication referred to herein is specifically incorporated by reference herein in its entirety.

What is claimed is:

1. A method of treating a patient with gastric cancer that overexpresses HER2, the method comprising administering to the patient, a HER2 directed therapy consisting of: an initial dose of 30 mg/m$^2$ (doxorubicin-HCl equivalent) of doxorubicin in MM302 doxorubicin HER-2 targeted immunoliposomes and 8 mg/kg trastuzumab, followed by the administration to the patient once every three weeks of 30 mg/m$^2$ (doxorubicin-HCl equivalent) of doxorubicin in the MM302 doxorubicin HER-2 targeted immunoliposomes and 6 mg/kg trastuzumab, to treat the gastric cancer.

2. The method of claim 1, wherein the gastric cancer is a locally advanced/unresectable or metastatic advanced gastric cancer.

3. The method of claim 1, wherein the gastric cancer characterized by overexpression of HER2 receptor is further characterized as being HER2 2+, HER2 3+, or HER2 FISH positive.

4. The method of claim 1, wherein the gastric cancer characterized by overexpression of HER2 receptor is further characterized as expressing an average of at least 200,000 cell surface HER2 receptors per cell.

5. The method of claim 1, wherein the MM302 doxorubicin HER-2 targeted immunoliposomes are administered intravenously over 60 minutes.

6. The method of claim 1, wherein the MM302 doxorubicin HER-2 targeted immunoliposomes are administered before the trastuzumab.

7. The method of claim 1, further comprising one or more of the following:
   a. the gastric cancer is a locally advanced/unresectable gastric cancer;
   b. the gastric cancer is a metastatic advanced gastric cancer;
   c. the gastric cancer characterized by expression of HER2 receptor is further characterized as being HER2 2+ prior to administering the MM302 doxorubicin HER-2 targeted immunoliposomes;
   d. the gastric cancer characterized by expression of HER2 receptor is further characterized as being HER2 3+ prior to administering the MM302 doxorubicin HER-2 targeted immunoliposomes;
   e. the gastric cancer characterized by expression of HER2 receptor is further characterized as being HER2 FISH positive prior to administering the MM302 doxorubicin HER-2 targeted immunoliposomes;

f. the gastric cancer characterized by overexpression of HER2 receptor is further characterized as expressing an average of at least 200,000 cell surface HER2 receptors per cell;
g. the MM302 doxorubicin HER-2 targeted immunoliposomes are administered intravenously over 60 minutes; and
h. the MM302 doxorubicin HER-2 targeted immunoliposome are administered before the trastuzumab.

8. A method of treating a patient diagnosed with locally advanced/unresectable gastric cancer or metastatic advanced gastric cancer having a HER2 imunohistochemistry (IHC) score of HER2 2+ or HER2 3+, the method comprising administering to the patient:
a. 30 mg/m$^2$ (doxorubicin-HCl equivalent) of doxorubicin in MM302 doxorubicin HER-2 targeted immunoliposomes in combination with 8 mg/kg trastuzumab, followed by
b. administering to the patient once every three weeks 30 mg/m$^2$ (doxorubicin-HCl equivalent) of doxorubicin in MM302 doxorubicin HER-2 targeted immunoliposomes in combination with 6 mg/kg trastuzumab, to treat the locally advanced/unresectable or metastatic advanced gastric cancer.

9. The method of claim 8, wherein the locally advanced/unresectable gastric cancer or metastatic advanced gastric cancer characterized by overexpression of HER2 receptor is further characterized as being HER2 FISH positive.

10. The method of claim 8, wherein the locally advanced/unresectable gastric cancer or metastatic advanced gastric cancer characterized by overexpression of HER2 receptor is further characterized as expressing an average of at least 200,000 cell surface HER2 receptors per cell.

11. The method of claim 8, wherein the MM302 doxorubicin HER-2 targeted immunoliposomes are administered intravenously over 60 minutes.

12. The method of claim 8, further comprising one or more of the following:
a. the gastric cancer is a locally advanced/unresectable gastric cancer;
b. the gastric cancer is a metastatic advanced gastric cancer;
c. the gastric cancer characterized by expression of HER2 receptor is further characterized as being HER2 2+ prior to administering the MM302 doxorubicin HER-2 targeted immunoliposomes;
d. the gastric cancer characterized by expression of HER2 receptor is further characterized as being HER2 3+ prior to administering the MM302 doxorubicin HER-2 targeted immunoliposomes;
e. the gastric cancer characterized by expression of HER2 receptor is further characterized as being HER2 FISH positive prior to administering the MM302 doxorubicin HER-2 targeted immunoliposomes;
f. the gastric cancer characterized by expression of HER2 receptor further characterized as expressing an average of at least 200,000 cell surface HER2 receptors per cell;
g. the MM302 doxorubicin HER-2 targeted immunoliposomes are administered intravenously over 60 minutes; and
h. the MM302 doxorubicin HER-2 targeted immunoliposome are administered before the trastuzumab.

13. A method of treating a patient diagnosed with gastric cancer, or locally advanced/unresectable gastric cancer or metastatic advanced gastric cancer, each of which is characterized as being HER2 FISH positive, the method comprising administering to the patient:
a. 35 mg/m$^2$ (doxorubicin-HCl equivalent) of doxorubicin in MM302 doxorubicin HER-2 targeted immunoliposomes in combination with 8 mg/kg trastuzumab, followed by
b. administering to the patient once every three weeks 35 mg/m$^2$ (doxorubicin-HCl equivalent) of doxorubicin in MM302 doxorubicin HER-2 targeted immunoliposomes in combination with 6 mg/kg trastuzumab, to treat the gastric cancer, or locally advanced/unresectable or metastatic advanced gastric cancer.

14. The method of claim 13, wherein the gastric cancer, or locally advanced/unresectable or metastatic advanced gastric cancer characterized as being HER2 FISH positive is further characterized by a HER2 imunohistochemistry (IHC) score of HER2 2+ or HER2 3+ prior to administration of the MM302 doxorubicin HER-2 targeted immunoliposomes.

15. The method of claim 13, wherein the gastric cancer, or locally advanced/unresectable gastric cancer or metastatic advanced gastric cancer characterized as being HER2 FISH positive expresses an average of at least 200,000 cell surface HER2 receptors per cell.

16. The method of claim 13, wherein the MM302 doxorubicin HER-2 targeted immunoliposomes are administered intravenously over 60 minutes.

17. The method of claim 13, wherein the gastric cancer, or locally advanced/unresectable gastric cancer is characterized by a HER2 imunohistochemistry (IHC) score of HER2 2+ or HER2 3+ prior to administration of the MM302 doxorubicin HER-2 targeted immunoliposomes.

18. The method of claim 17, wherein the gastric cancer, or locally advanced/unresectable gastric cancer is characterized by a HER2 imunohistochemistry (IHC) score of HER2 3+ prior to administration of the MM302 doxorubicin HER-2 targeted immunoliposome.

19. The method of claim 13, wherein the metastatic advanced gastric cancer is characterized by a HER2 imunohistochemistry (IHC) score of HER2 2+ or HER2 3+ prior to administration of the MM302 doxorubicin HER-2 targeted immunoliposomes.

20. The method of claim 19, wherein the metastatic advanced gastric cancer is characterized by a HER2 imunohistochemistry (IHC) score of HER2 3+ prior to administration of the MM302 doxorubicin HER-2 targeted immunoliposomes.

21. The method of claim 13, further comprising one or more of the following:
a. the gastric cancer is a locally advanced/unresectable gastric cancer;
b. the gastric cancer is a metastatic advanced gastric cancer;
c. the gastric cancer characterized by expression of HER2 receptor is further characterized as being HER2 2+ prior to administering the MM302 doxorubicin HER-2 targeted immunoliposome;
d. the gastric cancer characterized by expression of HER2 receptor is further characterized as being HER2 3+ prior to administering the MM302 doxorubicin HER-2 targeted immunoliposome;
e. the gastric cancer characterized by expression of HER2 receptor is further characterized as being HER2 FISH positive prior to administering the MM302 doxorubicin HER-2 targeted immunoliposome;
f. the gastric cancer characterized by expression of HER2 receptor further characterized as expressing an average of at least 200,000 cell surface HER2 receptors per cell;

g. the MM302 doxorubicin HER-2 targeted immunoliposomes are administered intravenously over 60 minutes; and h. the MM302 doxorubicin HER-2 targeted immunoliposome are administered before the trastuzumab.

22. A method of treating a patient with gastric cancer that overexpresses HER2, the method comprising administering to the patient, a HER2 directed therapy consisting of: an initial dose of 30 mg/m$^2$ (doxorubicin-HCl equivalent) of doxorubicin in MM302 doxorubicin HER-2 targeted immunoliposomes and 8 mg/kg trastuzumab, followed by the administration to the patient once every three weeks of 30 mg/m$^2$ (doxorubicin-HCl equivalent) of doxorubicin in the MM302 doxorubicin HER-2 targeted immunoliposomes and 6 mg/kg trastuzumab, to treat the gastric cancer, wherein the doses of MM302 doxorubicin HER-2 targeted immunoliposomes are formulated to contain 10.1 mL of MM-302 doxorubicin HER-2 targeted immunoliposomes at a concentration of 25 mg/mL in 20 mM histidine, 150 mM sodium chloride, and a final solution pH of 6.5.

* * * * *